US011364358B2

(12) United States Patent
Cortez, Jr. et al.

(10) Patent No.: US 11,364,358 B2
(45) Date of Patent: Jun. 21, 2022

(54) NASAL CANNULA FOR CONTINUOUS AND SIMULTANEOUS DELIVERY OF AEROSOLIZED MEDICAMENT AND HIGH FLOW THERAPY

(71) Applicant: Vapotherm, Inc., Exeter, NH (US)

(72) Inventors: Felino V. Cortez, Jr., Bowie, MD (US); Charles Busey, Easton, MD (US); George C. Dungan, II, Dallas, TX (US)

(73) Assignee: Vapotherm, Inc., Exeter, NH (US)

( * ) Notice: Subject to any disclaimer, the term of this patent is extended or adjusted under 35 U.S.C. 154(b) by 534 days.

(21) Appl. No.: 15/199,158

(22) Filed: Jun. 30, 2016

(65) Prior Publication Data

US 2017/0000965 A1 Jan. 5, 2017

Related U.S. Application Data

(60) Provisional application No. 62/187,095, filed on Jun. 30, 2015.

(51) Int. Cl.
*A61M 16/06* (2006.01)
*A61M 16/14* (2006.01)
(Continued)

(52) U.S. Cl.
CPC ........ *A61M 16/0666* (2013.01); *A61M 11/00* (2013.01); *A61M 11/02* (2013.01);
(Continued)

(58) Field of Classification Search
CPC .......... A61M 16/0666; A61M 16/0672; A61M 16/14; A61M 16/16; A61M 16/0683;
(Continued)

(56) References Cited

U.S. PATENT DOCUMENTS

| | | | |
|---|---|---|---|
| 4,422,456 | A | 12/1983 | Tiep |
| 4,782,832 | A | 11/1988 | Trimble et al. |

(Continued)

FOREIGN PATENT DOCUMENTS

| | | |
|---|---|---|
| AU | 2013212314 | 11/2017 |
| AU | 2013337995 | 6/2018 |

(Continued)

OTHER PUBLICATIONS

International Search Report dated Dec. 3, 2018, Application No. PCT/US2018/049979 (9 pages).
(Continued)

*Primary Examiner* — Joseph D. Boecker
*Assistant Examiner* — Brian T Khong
(74) *Attorney, Agent, or Firm* — White & Case LLP

(57) ABSTRACT

Systems, devices, and methods are disclosed for nasal cannulas allowing simultaneous flow of humidified breathing gas and aerosolized medicament for use in respiratory therapy. Utilizing separate flow paths and separate cannula outlets for the heated and humidified breathing gas and for the aerosolized medicament, these systems, methods, and devices reduce condensation of the aerosolized medicament by delaying mixing of the flow of aerosolized medicament and the flow of heated and humidified breathing gas until the flows exit the cannula.

40 Claims, 9 Drawing Sheets

(51) Int. Cl.

| | | |
|---|---|---|
| *A61M 11/00* | (2006.01) | |
| *A61M 11/02* | (2006.01) | |
| *A61M 16/16* | (2006.01) | |
| *A61M 16/12* | (2006.01) | |
| *A61M 16/00* | (2006.01) | |
| *A61M 16/10* | (2006.01) | |
| *A61M 11/06* | (2006.01) | |

(52) U.S. Cl.
CPC ........ *A61M 16/0672* (2014.02); *A61M 16/14* (2013.01); *A61M 16/16* (2013.01); *A61M 11/005* (2013.01); *A61M 11/06* (2013.01); *A61M 16/0063* (2014.02); *A61M 16/1075* (2013.01); *A61M 16/12* (2013.01); *A61M 16/125* (2014.02); *A61M 2202/0208* (2013.01); *A61M 2205/36* (2013.01)

(58) Field of Classification Search
CPC ............ A61M 16/1095; A61M 16/208; A61M 16/0875; A61M 16/1075; A61M 16/08; A61M 16/0677; A61M 11/02; A61M 2205/36; A61M 2205/3368

See application file for complete search history.

(56) References Cited

U.S. PATENT DOCUMENTS

| | | | |
|---|---|---|---|
| 4,790,308 A | 12/1988 | Weichselbaum | |
| 5,099,836 A | 3/1992 | Rowland et al. | |
| 6,805,126 B2* | 10/2004 | Dutkiewicz | A61M 16/0666 128/207.18 |
| 6,986,353 B2* | 1/2006 | Wright | A61M 16/0672 128/207.18 |
| 7,007,694 B2 | 3/2006 | Aylsworth et al. | |
| 7,743,770 B2* | 6/2010 | Curti | A61M 16/085 128/207.18 |
| 7,832,400 B2 | 11/2010 | Curti et al. | |
| 9,333,317 B2 | 5/2016 | Cortez, Jr. et al. | |
| 9,925,348 B2 | 3/2018 | Payton et al. | |
| 10,265,494 B2 | 4/2019 | Cortez, Jr. et al. | |
| 10,300,236 B2 | 5/2019 | Cortez, Jr. et al. | |
| 2004/0112383 A1 | 6/2004 | Curti et al. | |
| 2004/0226566 A1 | 11/2004 | Gunaratnam et al. | |
| 2005/0028822 A1 | 2/2005 | Sleeper et al. | |
| 2005/0066976 A1* | 3/2005 | Wondka | A61M 16/06 128/207.18 |
| 2005/0103347 A1 | 5/2005 | Curti et al. | |
| 2005/0229927 A1 | 10/2005 | Fink et al. | |
| 2006/0030696 A1 | 2/2006 | Bonnerjea et al. | |
| 2006/0230929 A1* | 10/2006 | Bliss | B01D 53/0407 95/96 |
| 2006/0230931 A1* | 10/2006 | Bliss | B01D 53/0407 95/130 |
| 2007/0175473 A1 | 8/2007 | Lewis et al. | |
| 2008/0121230 A1 | 5/2008 | Cortez et al. | |
| 2008/0223375 A1* | 9/2008 | Cortez | A61M 16/0688 128/207.18 |
| 2009/0044808 A1* | 2/2009 | Guney | A61M 16/0605 128/206.24 |
| 2009/0101147 A1* | 4/2009 | Landis | A61M 16/0666 128/204.18 |
| 2009/0253995 A1 | 10/2009 | Lewis et al. | |
| 2010/0108073 A1 | 5/2010 | Zollinger et al. | |
| 2010/0113955 A1* | 5/2010 | Colman | A61M 16/0666 600/532 |
| 2010/0252037 A1* | 10/2010 | Wondka | A61M 16/0666 128/203.12 |
| 2010/0282247 A1 | 11/2010 | Kadrichu et al. | |
| 2011/0067704 A1 | 3/2011 | Kooij et al. | |
| 2011/0094518 A1* | 4/2011 | Cipollone | A61M 16/0666 128/207.18 |
| 2011/0146685 A1 | 6/2011 | Allan et al. | |
| 2011/0232649 A1 | 9/2011 | Collazo et al. | |
| 2011/0284001 A1* | 11/2011 | Tero | A61M 16/0666 128/204.18 |
| 2012/0090622 A1 | 4/2012 | Chang | |
| 2012/0125332 A1* | 5/2012 | Niland | A61M 16/00 128/203.16 |
| 2012/0167878 A1* | 7/2012 | Belson | A61F 7/12 128/200.16 |
| 2012/0304992 A1* | 12/2012 | Ratto | A61M 16/0666 128/203.26 |
| 2013/0008447 A1 | 1/2013 | Gunaratnam et al. | |
| 2013/0092165 A1* | 4/2013 | Wondka | A61M 15/08 128/204.25 |
| 2013/0152925 A1 | 6/2013 | Rahmel et al. | |
| 2013/0160772 A1* | 6/2013 | Tabrizchi | A61M 16/0666 128/207.18 |
| 2013/0186395 A1* | 7/2013 | Cortez, Jr. | A61M 16/14 128/203.12 |
| 2014/0066801 A1* | 3/2014 | Tero | A61M 16/0666 600/543 |
| 2014/0116447 A1* | 5/2014 | Cortez, Jr. | A61M 16/0666 128/207.18 |
| 2014/0137744 A1* | 5/2014 | Wilkinson | B01D 53/047 96/152 |
| 2014/0147506 A1 | 5/2014 | Longest et al. | |
| 2014/0150789 A1* | 6/2014 | Flanagan | A61M 16/10 128/203.22 |
| 2014/0158127 A1* | 6/2014 | Boucher | A61M 16/0683 128/203.22 |
| 2014/0166009 A1 | 6/2014 | Flanagan et al. | |
| 2014/0261704 A1* | 9/2014 | Hoogenakker | G05D 16/00 137/1 |
| 2014/0366885 A1 | 12/2014 | Haibach et al. | |
| 2015/0000654 A1* | 1/2015 | Martin | A61M 16/12 128/203.12 |
| 2015/0000659 A1* | 1/2015 | Martin | A61M 16/0672 128/203.22 |
| 2015/0000660 A1* | 1/2015 | Martin | A61M 16/0672 128/203.22 |
| 2015/0090255 A1* | 4/2015 | Gulliver | A61J 15/0053 128/202.15 |
| 2015/0230731 A1* | 8/2015 | Levitsky | A61B 5/097 600/532 |
| 2016/0015296 A1* | 1/2016 | Garaycochea | A61B 5/097 600/531 |
| 2016/0015921 A1 | 1/2016 | Harrison et al. | |
| 2016/0158476 A1* | 6/2016 | Tatkov | A61M 16/0688 128/203.22 |
| 2019/0328990 A1 | 10/2019 | Cortez et al. | |
| 2019/0328993 A1 | 10/2019 | Cortez et al. | |

FOREIGN PATENT DOCUMENTS

| | | |
|---|---|---|
| AU | 2017251790 | 3/2020 |
| EP | 2022528 A2 | 2/2009 |
| EP | 2247331 A1 | 11/2010 |
| EP | 2806926 | 5/2017 |
| EP | 2914322 | 12/2018 |
| EP | 3646913 | 5/2020 |
| EP | 3216475 | 7/2020 |
| EP | 3747488 | 12/2020 |
| FR | 2827778 A1 | 1/2003 |
| WO | WO-9818513 | 5/1998 |
| WO | WO-2006138579 | 12/2006 |
| WO | WO-2008060587 A2 | 5/2008 |
| WO | WO-2013041996 A2 | 3/2013 |
| WO | WO-2013042004 A1 | 3/2013 |
| WO | WO-2013112545 | 8/2013 |
| WO | WO-2013157960 A1 | 10/2013 |
| WO | WO-2014070833 | 5/2014 |
| WO | WO-2014142681 A1 | 9/2014 |
| WO | WO-2015121815 A1 | 8/2015 |
| WO | WO-2015164921 A1 | 11/2015 |
| WO | WO-2016043607 A1 | 3/2016 |
| WO | WO-2018005851 A1 | 1/2018 |

(56) References Cited

FOREIGN PATENT DOCUMENTS

WO    WO-2018065588     4/2018
WO    WO-2019191814    10/2019

OTHER PUBLICATIONS

International Search Report dated Oct. 18, 2017, Application No. PCT/US2017/040079 (21 pages).
International Search Report dated Oct. 4, 2016, Application No. PCT/US2016/040465 (16 pages).
International Search Report dated Oct. 7, 2020, Application No. PCT/US2020/039641 (13 pages).
Doshi et al., "High-Velocity Nasal Insufflation in the Treatment of Respiratory Failure: A Randomized Clinical Trial", Annals of Emergency Medicine, Jul. 2017;72(1):73-83.
Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).

\* cited by examiner

1500

1502

Pass Heated and Humidified Breathing Gas Through a First Conduit to a First Outlet and a Second Outlet of a Nasal Cannula

1504

Pass Aerosolized Medicament Through a Second Conduit to a Third Outlet of a Nasal Cannula

FIG. 15

NASAL CANNULA FOR CONTINUOUS AND SIMULTANEOUS DELIVERY OF AEROSOLIZED MEDICAMENT AND HIGH FLOW THERAPY

CROSS REFERENCE TO RELATED APPLICATIONS

This application claims the benefit of U.S. Provisional Application No. 62/187,095, filed on Jun. 30, 2015, which is hereby incorporated herein by reference in its entirety.

BACKGROUND

Patients with respiratory ailments may be treated with respiratory assist devices that deliver supplemental breathing gas to a patient. In some instances, respiratory assist devices may be used for high flow therapy ("HFT"). During HFT, a high flow rate of breathing gas (typically 8 liters per minute ("LPM") or greater) is delivered to a patient via a nasal cannula to increase a patient's fraction of inspired oxygen (FiO2), while simultaneously decreasing a patient's work of breathing. Additionally, some HFT devices may heat and humidify the delivered breathing gas to reduce patient discomfort.

Patients using respiratory assist devices may also benefit from administration of nebulized medications. Nebulizers allow aerosolized liquid and powder respiratory medications, such as bronchodilators (e.g., Albuterol (Ventolin®), Salbutamol (Proventil®), Levosalbutamol/Levalbuterol (Xopenex®)) for treating asthma or Chronic Obstructive Pulmonary Disease ("COPD") to be administered through inhalation directly into a patient's lungs. Nebulizers may be connected to respiratory assist devices to supply nebulized medication together with supplemental breathing gas. Such systems can allow a patient to receive the medication without stopping use of a respiratory assist device.

In some cases, a combination of nebulized medication and HFT can be used to assist patients experiencing respiratory distress and provide a comfortable and effective management of cardiopulmonary conditions. A challenge associated with delivering nebulized medication via a high-flow system is the condensation of moisture from the mixture of heated and humidified breathing gas and nebulized medication. Condensation in a ventilation circuit presents both clinical and mechanical challenges, as the condensate can build up to limit flow through the system and also collect and stagnate, which presents a biologic hazard to the patient.

SUMMARY

Disclosed herein are systems, methods, and devices for nasal cannulas allowing simultaneous delivery of breathing gas and aerosolized (e.g., nebulized) medicament to a patient's nares during respiratory therapy. Utilizing separate flow paths and separate cannula outlets for the heated and humidified breathing gas and for the aerosolized medicament, these systems, methods, and devices reduce condensation of the aerosolized medicament by delaying mixing of the flow of aerosolized medicament and the flow of heated and humidified breathing gas until the flows exit the cannula. The heated and humidified breathing gas may mix with the aerosolized medicament within the nares of a patient or proximal to the nares of a patient after exiting the cannula. For example, by delaying the mixing of the flows, these systems, methods, and devices prevent a drop in the temperature of the heated and humidified breathing gas as the heated and humidified breathing gas flows through the respiratory therapy system. By preventing this temperature drop, condensation of the humidity from the breathing gas is reduced or avoided. Since nebulized medicament tends to condense together with condensed moisture in the heated and humidified breathing gas, preventing the condensation in the breathing gas also prevents condensation and subsequent waste of the nebulized medicament. Thus, by delaying the mixing of the flows, these systems, methods, and devices increase the overall efficiency of medicament delivery by reducing the condensate that can build up to limit flow through the system and also collect and stagnate, which presents a biologic hazard to the patient.

Furthermore, the systems provide a non-intrusive, low profile interface without sacrificing the efficiency of the medicament delivery. For example, instead of physically coupling the nebulizer directly to a facepiece of a nasal cannula, the systems, methods, and devices allow the nebulizer to be moved away from the patient (e.g., >20 cm, >40 cm, >60 cm, >80 cm, >1 m, >3 m away). This separation (i) allows a caregiver to interact with the nebulizer (e.g., change or refill medication, power the nebulizer on or off, or change the settings of the nebulizer) without having to reach uncomfortably close to the patient's face; (ii) affords the patient a greater range of activities during therapy (e.g., eating or drinking); and (iii) reduces the amount of noise from the nebulizer that reaches the patient, thus providing a quieter environment for the patient.

Moreover, providing heated breathing gas in parallel with aerosolized medicament increases the temperature of the gas inhaled by the patient compared to delivery of aerosolized medicament alone (e.g., by 0.5° C., 1° C., 2° C., 5° C., 10° C., or greater). The increase in temperature of the aerosolized medicament brings the temperature of the medicament closer to the patient's temperature before inhalation and decreases the temperature gradient between the patient's nostrils and the incoming flow. This reduces or eliminates a potentially unpleasant cool feeling inside the patient's nostrils, which improves the comfort of the patient during treatment.

In one aspect, a nasal cannula for delivering humidified breathing gas and aerosolized medication includes a first prong with a first outlet, in which the first outlet has a longitudinal axis, and a length along the longitudinal axis. The nasal cannula also includes a second prong with a second outlet. The nasal cannula also includes a first medicament outlet disposed adjacent to the first prong and arranged to pass aerosolized medicament substantially parallel to the longitudinal axis. The nasal cannula also includes a first tube with an inlet for receiving breathing gas, which is in fluid communication with the first and second prongs. The nasal cannula also includes a second tube with an inlet for receiving aerosolized medicament, which is in fluid communication with the first medicament outlet, and in which the first tube is not in fluid communication with the second tube along the length of the second tube.

In certain implementations, the first medicament outlet is offset from the first outlet along the longitudinal axis in order to improve efficiencies. For example, in certain implementations, the first medicament outlet is offset from the first outlet with respect to a direction of breathing gas flow through the first outlet. For example, the first medicament outlet may be upstream from the first outlet with respect to the direction of breathing gas flow through the first outlet. The amount of the offset may vary. For example, the first medicament outlet may be offset by more than about 1 mm and less than about 3 cm along the longitudinal axis.

Additionally or alternatively, the arrangement of the first outlet, the second outlet, and the first medicament outlet may vary. For example, in certain implementations, the first medicament outlet is substantially concentric with the first outlet, while in other implementations, the first medicament outlet is not substantially concentric with the first outlet. In certain implementations, the first medicament outlet includes a third prong having a third length. The length of the third prong may vary. For example, the third length may be less than, equal to, or greater than the first length. In some implementations, the third prong extends along the first prong and shares a common border with the first prong. Additionally or alternatively, in some implementations, the nasal cannula may include a plurality of medicament outlets. For example, the nasal cannula may include a second medicament outlet disposed adjacent to the second prong and arranged to pass aerosolized medicament substantially parallel to the longitudinal axis.

In some implementations, the first prong and the second prong extend from a facepiece, which may allow for more intuitive, ergonomic, and direct application of the treatment. For example, the facepiece may be substantially orthogonal to the longitudinal axis and have a first end and a second end opposite, the first end. In some implementations, the first tube is coupled to the first end and the second tube is coupled to the second end. In other implementations, the first tube is coupled to each of the first and second ends. In some implementations the medicament outlet is disposed on the facepiece between the first prong and the second prong.

The dimensions of the first tube and the second tube may vary. For example, in some implementations, the first and/or second tube may have an internal diameter of about 5 mm or more. In other implementations, the first and/or second tube may have an internal diameter of about 10 mm or more. In some implementations, the first and/or second tubes have a length of about 20 cm or more. In some implementations, the first and/or second tubes have an internal volume of about 20 cm$^3$ or greater. In other implementations, the first and/or second tubes have an internal volume of about 70 cm$^3$ or greater.

The cross-sectional areas of the first outlet, second outlet, and medicament outlet may also vary. For example, in certain implementations, the first outlet of the nasal cannula has a first cross-sectional area, and the first medicament outlet has a second cross-sectional area, wherein the second cross-sectional area is less than (or greater than) the first cross-sectional area. For example, the second cross-sectional area may be about one third of the first cross-sectional area or greater. The flow resistance from the second inlet to the first medicament outlet may vary. For example, in some implementations, the flow resistance from the second inlet to the first medicament outlet is less than 1 psi at a flow rate of 1 LPM.

In another aspect, a method for delivering humidified breathing gas and nebulized medication includes passing heated and humidified breathing gas through a first conduit to a first outlet and a second outlet of a nasal cannula, passing an aerosolized medicament through a second conduit to a third outlet, wherein the third outlet is adjacent to the first outlet and aligned substantially parallel to the first outlet, and wherein that the heated and humidified breathing gas mixes with the aerosolized medicament after exiting the nasal cannula. In some implementations, the length of the first and/or second conduit may vary. For example, the first and/or second conduit may have a length of about 10 cm or greater. In some implementations, the second conduit is not in fluid communication with the first conduit along the length of the first conduit. In certain implementations, the third outlet is offset from the first outlet along a longitudinal axis of the first outlet.

In certain implementations, the aerosolized medicament is entrained by the flow of heated and humidified breathing gas out of the first outlet. In some implementations, the heated and humidified breathing gas is passed through the first conduit at a rate of about 8 LPM or greater. In some implementations, the aerosolized medicament is passed through the second conduit at a rate of about 2 LPM or less. In certain implementations, an inlet of the first conduit is adjacent to an inlet of the second conduit.

In another aspect, the respiratory therapy system for delivering humidified breathing gas and nebulized medication includes a nasal cannula and a nebulizer. The nasal cannula includes a first prong having a first outlet and a longitudinal axis; a second prong having a second outlet; a first medicament outlet disposed adjacent to the first prong and arranged to pass aerosolized medicament substantially parallel to the longitudinal axis; a first tube in fluid communication with the first and second prongs; and a second tube having a second length, wherein the first tube is not in fluid communication with the second tube along the length of the first tube. The nebulizer is in fluid communication with the first medicament outlet through the second tube.

In some implementations, the respiratory therapy system further includes a source of pressurized driving gas in fluid communication with the second tube, wherein the source of pressurized driving gas supplies gas that carries the aerosolized medicament to the patient. In certain implementations, the respiratory therapy system also includes a source of heated and humidified breathing gas in fluid communication with the first and second prongs. In certain implementations, the first medicament outlet is offset from the first outlet along the longitudinal axis. In some implementations, the first medicament outlet is substantially concentric with the first outlet.

In some implementations, the respiratory therapy system includes a second medicament outlet disposed adjacent to the second prong and arranged to pass aerosolized medicament substantially parallel to the longitudinal axis. In some implementations, the first prong and the second prong extend from a facepiece, the facepiece being substantially orthogonal to the longitudinal axis and having a first end and a second end opposite the first end. In some implementations, the first tube is coupled to the first end and the second tube is coupled to the second end. In other implementations, the first tube is coupled to each of the first and second ends. In certain implementations, the second tube has an internal diameter of about 5 mm or more. In some implementations, the second tube has a length of about 2 feet or more. In some implementations, the second tube has an internal volume of about 20 cm$^3$ or greater.

Variations and modifications will occur to those of skill in the art after reviewing this disclosure. The disclosed features may be implemented, in any combination and subcombination (including multiple dependent combinations and subcombinations), with one or more other features described herein. For example, any of the nasal cannulas described herein having a single medicament outlet may include two medicament outlets (e.g., one for each breathing gas prong). Similarly, any of the nasal cannulas described herein may be implemented with a guiding element such as a hood, a bill, or a groove to facilitate the slipstream effect. Furthermore, while certain implementations are discussed with regard to high flow therapy ("HFT"), it should be noted that the systems, methods, and devices are not necessarily limited to HFT. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 15 shows an illustrative process for delivering heated and humidified gas and aerosolized medicament to a patient.

DETAILED DESCRIPTION

Figure 1:
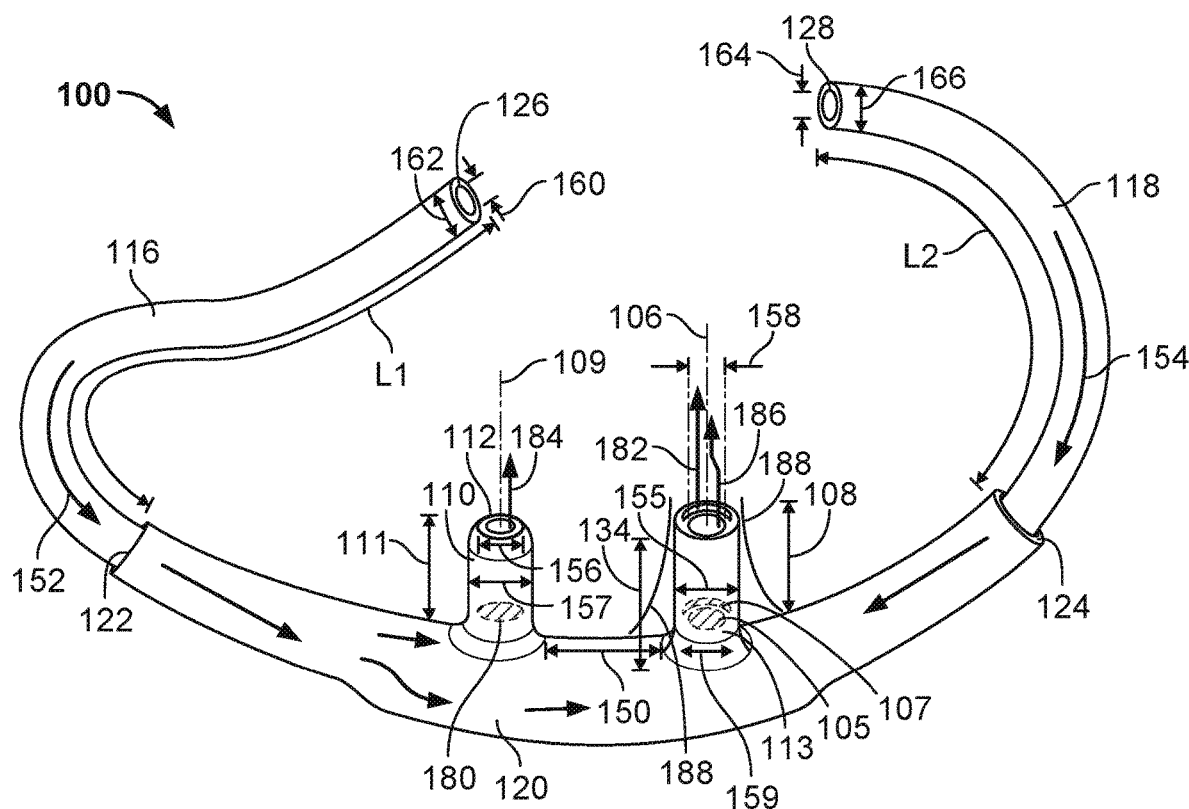
FIG. 1 shows an illustrative nasal cannula for simultaneously delivering breathing gas and aerosolized medicament.

To provide an overall understanding of the systems, devices, and methods described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, and tracheotomy masks.

The systems, devices and methods described herein provide a nasal cannula that allows simultaneous administration of aerosolized medicament and respiratory therapy. The nasal cannula allows for delivery of both breathing gas and aerosolized medicament by separate flow paths and separate cannula outlets that are not in fluid communication with each other. Separation of the flow of breathing gas and aerosolized medicament is beneficial because it prevents cooling of the humidified gas which could lead to condensation of moisture from the humidified gas. Condensation of the moisture may be undesirable because condensate tends to nucleate around the particles of aerosolized medicament, thus removing the particles from the gas in which they are suspended. Therefore, preventing or reducing condensation by separating the flow of aerosolized medicament and heated and humidified breathing gas prevents or reduces the loss of the aerosolized medicament. Preventing or reducing the loss of aerosolized medicament increases the efficiency of therapy and enables more accurate calculation of the effective dosage of medicament received by the patient during therapy.

The systems, methods, and devices also improve patient comfort by locating the nebulizer and the gas source at a distance from the patient (e.g., 5 ft, 10 ft, 15 ft, 20 ft, or any other suitable length), rather than near or on the patient. This reduces the noise that reaches the patient from the gas source or the nebulizer (e.g., due to gas compressors). Additionally, placement of the nebulizer and gas source at a distance from the patient reduces bulk around the patient, particularly around the patient's face. This placement is enabled by the reduction in condensation achieved by separating the flow paths. Since less condensation occurs, more of the medicament can travel a longer distance through tubing without depositing onto the sides of the tubing.

The length of tubing between the nebulizer and the cannula can also improve delivery of the medicament by providing a hanging volume (i.e., the volume of tubing through which the aerosol travels). The hanging volume stabilizes the aerosol particles by filtering out large aerosol particles which adhere to the interior of the tubing along its length. Filtering out the larger particles can be desirable because large aerosol particles tend to deposit in the patient's upper respiratory tract, which can cause patient discomfort, instead of traveling to the lower airways, where the medicament is typically most effective. Thus, the hanging volume provided by the length of tubing can improve the delivery of medicament by stabilizing the aerosol.

Additionally, providing heated and humidified breathing gas to the patient along with the aerosol can increase patient comfort by counterbalancing the cooling and drying sensations associated with the delivery of aerosol to the nare. This is because the heated and humidified breathing gas warms the aerosolized medicament, causing the patient to feel less of a temperature gradient than when aerosol alone is provided. The heated and humidified breathing gas may also produce a wake or a slipstream that helps direct the aerosolized medicament toward the patient's nare. This can increase the percentage of medication delivered to the point of respiration and decrease the amount of medication which does not enter the nare.

Figure 2:
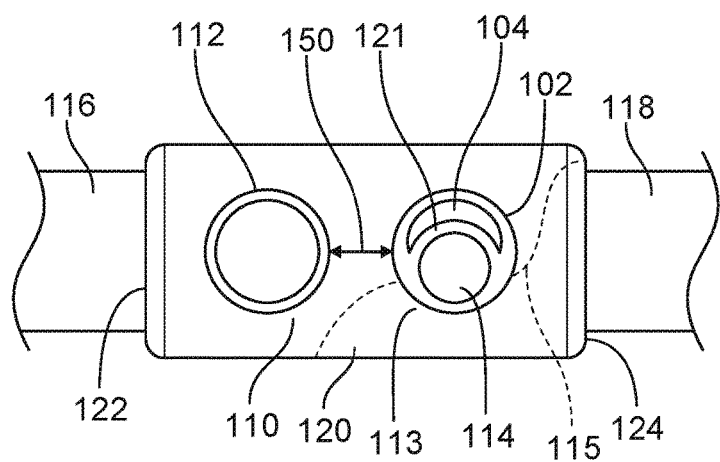
FIG. 2 shows a top view of the nasal cannula of FIG. 1.

FIG. 1 shows a nasal cannula 100 for simultaneously delivering breathing gas and aerosolized medicament, and FIG. 2 shows a top view of the nasal cannula 100. The nasal cannula 100 includes a facepiece 120, a first prong 102 with a first outlet 104, a second prong 110 with a second outlet 112, and a third prong 113 with a medicament outlet 114. The facepiece 120 is connected to a first tube 116 having a length L1 at a first end 122 and to a second tube 118 having a length L2 at a second end 124. The first tube 116 has an inner diameter 160 and an outer diameter 162. The first tube 116 provides a flow of heated and humidified breathing gas 152 from an inlet 126 to the first prong 102 and second prong 110. The flow of heated and humidified breathing gas 152 exits from the first outlet 104 of the first prong 102 as flow 182, and from the second outlet 112 of the second prong 110 as flow 184. The second tube 118 supplies an aerosolized medicament 154 from second inlet 128 through the second tube 118 to the medicament outlet 114. The aerosolized medicament 154 and the humidified breathing gas 152 are kept separate within the facepiece 120 by partition 115 (shown in FIG. 2) until exiting the cannula 100 into the nares.

The first prong 102 has a longitudinal axis 106 and a height 108 in the direction of the longitudinal axis 106, and the second prong 110 has a longitudinal axis 109 and a height 111 in the direction of the longitudinal axis 109. The first prong 102 and second prong 110 are oriented so that the flow of heated and humidified breathing gas 152 from each is directed substantially along the longitudinal axes 106 and 109, respectively. The outlet 104 of the first prong 102 has an inner diameter 153, an outer diameter 155, and a cross-sectional area 105. Similarly, the outlet 112 of the second prong 110 has an inner diameter 156, an outer diameter 157, and a cross-sectional area 180. The outer diameters 155 and 157 of the first and second prongs 102 and 110 may be selected so as not to occlude the patient's nare to facilitate exhalation and increase patient comfort. Preferably, the outer diameters 155 and 157 are determined so as to block about 50% of the nare or less (e.g., 40%, 30%, 20%, or less). For example, the prongs 102 and 110 may have an outer diameter of 8 mm or less (e.g., 7 mm, 6 mm, 5 mm, 4 mm, 3 mm, 2 mm). In some implementations, the outer diameter 155 of the first prong 102 is equal to the outer diameter 157 of the second prong 110. In other implementations, the outer diameter 155 of the first prong 102 and the outer diameter 157 of the second prong 110 are different. For example, in certain implementations, the outer diameter 155 of the first prong 102 is decreased to accommodate the placement and size of the medicament outlet 114 so that the combined size of the first prong 102 and third prong 113 do not occlude the patient's nare. Although diameters of the outlets 104 and 112 are discussed, in some implementations, the outlets 104 and 112 have non-circular cross-sections. The first prong 102 and the second prong 110 are separated on the facepiece 120 by a distance 150 selected for patient comfort. Similarly, the heights 108 and 111 of the first prong 104 and second prong 110 are selected so that the prongs 102 and 110 enter the patient's nares without causing discomfort.

The third prong 113 extends alongside of the first prong 102 and shares a common wall 121 (shown in FIG. 2) with the first prong 102. The third prong 113 includes the medicament outlet 114, which supplies aerosolized medicament 186 in a direction substantially parallel to the longitudinal axis 106 of the first prong 102. The medicament outlet 114 has an inner width 158, an outer width 159, and a cross-sectional area 107. The cross section of the medicament outlet 114 is substantially crescent-shaped and complements the cross section of the first prong 102. The close positioning of the medicament outlet 114 against the outlet 104 of the first prong 102 facilitates the entrainment of the aerosolized medicament 186 into the flow of humidified breathing gas 182. The cross-sectional area 107 of the medicament outlet 114 and the cross-sectional area 105 of the first outlet 104 are together about equal to the cross-sectional area 180 of the second prong 110. This configuration allows the obstructed area of each of a patient's nares to be about the same, while not greatly throttling the first outlet 104 relative to the second outlet 112. While a crescent-shaped cross section of the medicament outlet 114 is shown, in certain implementations, the cross section may be circular, rectangular, or any other suitable shape.

The cross-sectional area 107 of the medicament outlet 114 is less than the first cross sectional area 105 of the first outlet 104. In certain implementations, the second cross-sectional area 107 is about one third of the first cross-sectional area 105 or greater. This can prevent the flow resistance of aerosolized medicament from being excessively high, which could limit the delivery of aerosol or potentially alter the aerosol characteristics. While the medicament outlet 114 is located dorsal to the first prong 102 in cannula 100, in some implementations, the medicament outlet 114 may be located dorsally to the second prong 110, ventrally to either of the prongs 102 or 110, between the prongs 102 and 110, or in any other acceptable position. Similarly, although the medicament outlet 114 is shown as located on a separate third prong 113, the medicament outlet 114 may also be formed as an opening in the facepiece 120, positioned within the first or second prongs 102 or 110, or positioned in any other acceptable location.

The heated and humidified breathing gas 152 may be delivered through the first tube 116 at a rate of 8 LPM or greater (e.g., 10 LPM, 12 LPM, 14 LPM, 16 LPM, 40 LPM, etc.), while the aerosolized medicament may be delivered at a rate of 2 LPM or less (e.g., 1.5 LPM, 1 LPM, 0.5 LPM). This difference in volume flow rates causes the velocity of humidified breathing gas 182 exiting the first outlet 104 to be significantly higher than the velocity of aerosolized medicament 186 out of the medicament outlet 114. This difference in exit velocities produces a slipstream 188 around the first outlet 104. The slipstream 188 carries the aerosolized medicament 186 into the patient's nare with the humidified breathing gas 182. The use of the slipstream 188 allows the medicament outlet 114 to deliver the aerosolized medicament 186 to the patient's nares without being inserted into the patient's nares. Maintaining the medicament outlet 114 and third prong 113 outside the patient's nares decreases the area of the nares which is occluded, which may improve patient comfort and facilitate exhalation. For this reason, height 134 of the third prong 113 is less than height 108 of the first prong 102, which causes an offset between the medicament outlet 114 and the first outlet 104 along the longitudinal axis 106. The offset between the first outlet 104 and the medicament outlet 114 may be 1 mm, 2 mm, 4 mm, 5 mm, 10 mm, or any suitable distance.

In use, the aerosolized medicament can be provided by a nebulizer (not shown), such as a jet nebulizer or a vibrating mesh nebulizer. The aerosolized medicament may also include corticosteroids, antibiotics, opioid analgesics, or any other type of medicament amendable to respiratory delivery. Once generated, the aerosolized medicament 154 travels a length L2 through the second tube 118. The aerosolized medicament may be driven by a compressed gas through the second tube 118 to the medicament outlet 114. While only one tube (e.g., second tube 118) is shown, the second tube may include two or more tubes connected in series which span the distance between the source of aerosolized medicament and the nasal cannula 100. The second tube 118 has an inner diameter 164 and an outer diameter 166. The inner diameter 164 of the second tube 118 may be 5 mm or more.

In some implementations, the inner diameter 164 of the second tube 118 may be 10 mm or more over a portion of its length. The length L2 of the second tube 118 may be 20 cm or more. The flow resistance through the second tube 118 from the second inlet 128 to the medicament outlet 114 is less than 1 psi at a flow rate of 1 LPM (e.g., 0.5 psi, 0.25 psi, or 0.1 psi). In some implementations, the flow rate of aerosolized medicament during operation is 2 LPM or less. In certain implementations, the flow rate may be lower than 1 LPM, such as 0.25, 0.5, or 0.75 LPM.

The internal volume of the second tube 118 along its length L2 functions as a holding chamber and provides a hanging volume for the aerosol. This hanging volume improves the delivery of the aerosolized medicament 154 by filtering out larger aerosol particles which are more likely to adhere to the interior of the second tube 118. This filtering can be beneficial because the larger particles may be unable to travel into the patient's lower airways where the medicament is often needed most. The larger particles can tend to deposit in a patient's upper respiratory tract (e.g., nostrils, mouth, and throat), causing patient discomfort. Thus, the hanging volume provided by the second tube 118 can improve drug delivery by stabilizing the aerosol. In some implementations, the second tube 118 has an internal volume of 20 cm$^3$ or greater. In certain implementations, the second tube 118 has an internal volume of 70 cm$^3$ or greater. After the aerosolized medicament 154 exits the hanging volume of the second tube 118, the aerosolized medicament 154 enters the facepiece 120.

When the aerosolized medicament 154 and the heated and humidified gas 152 enter the facepiece 120, the flows are kept separate by partition 115 (shown in FIG. 2) within the facepiece 120. Partition 115 directs each flow to its respective outlet and keeps the aerosol and heated and humidified gas from fluid communication. In this way, the medicament and heated gas are kept separate from one another until the medicament 154 exits the medicament outlet 114 when mixing of the medicament 154 and heated and humidified gas 152 occurs in or just below the nares. By keeping the flow path of the aerosolized medicament 154 separate from the flow path of the heated and humidified gas 152, rapid cooling of the heated and humidified gas 152 is prevented. Preventing the rapid cooling of the heated and humidified gas 152 reduces or prevents condensation of moisture from the heated and humidified gas 152. Condensation of moisture from the heated and humidified gas tends to nucleate around the suspended aerosolized medicament 154, thus pulling the aerosolized medicament out of the gas flow. Therefore, preventing this condensation by keeping the flow aerosolized medicament 154 separate from the flow of the heated and humidified gas preserves the aerosolized medicament 154 in the suspended aerosol form. This allows a higher effective dosage of the medication to be delivered to the patient. Furthermore, the decreased waste of medication allows the source of aerosolized medicament to be located farther from the patient, thus increasing patient comfort. The reduction in condensation also makes the cannula 100 easier to use as frequent emptying of condensate is not required. Furthermore, the medication dosage received by the patient can be more accurately calculated since less medication is wasted.

Additionally, the delivery of the aerosolized medicament 154 and the heated and humidified breathing gas 152 by separate tubes allows a source of the aerosolized medicament 154 (e.g., a nebulizer) to be disconnected without interrupting the delivery of the heated and humidified breathing gas. Unlike systems that use a T or Y adaptor to connect a nebulizer to a respiratory therapy circuit, the cannula 100 involves no junction point between the flow of aerosolized medicament and the flow of breathing gas. Thus, removal of the source of aerosolized medicament does not introduce another opening in the breathing gas circuit. Thus, the source of aerosolized medicament can be simply removed without having to place a plug or cap in its place.

Furthermore, delivering heated and humidified gas 152 together with the aerosolized medicament 154 can increase patient comfort compared to delivering the aerosolized medicament 154 alone. This is because the heated and humidified breathing gas 152 mixes with the aerosolized medicament 154 as both flows exit the cannula 100, thus increasing the temperature of the aerosolized medicament 154. Since the temperature of the mixture is closer to the patient's body temperature compared to the aerosolized medicament alone, the sensation of a temperature gradient in the nare is decreased.

Figure 3:
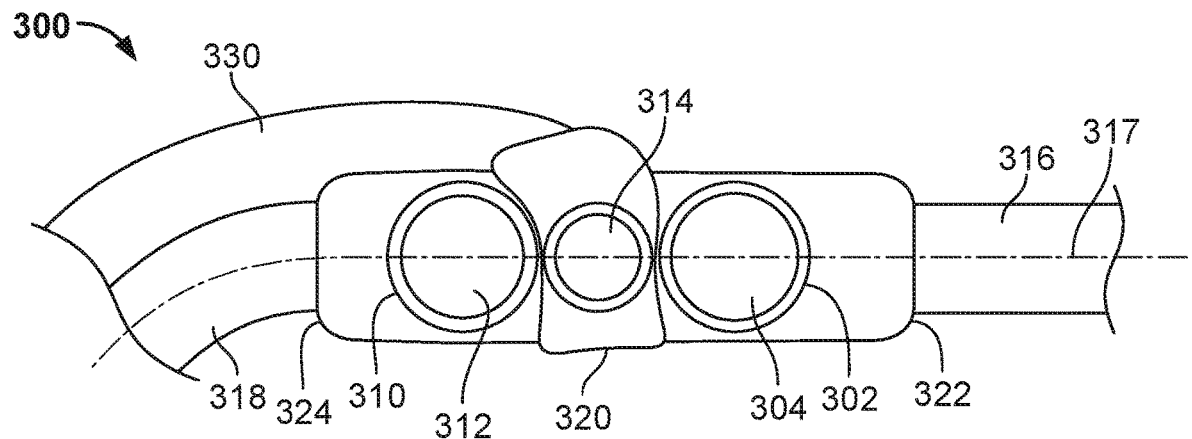
FIG. 3 shows an illustrative nasal cannula having a medicament outlet formed as a slit in a facepiece between two prongs.
Figure 4:
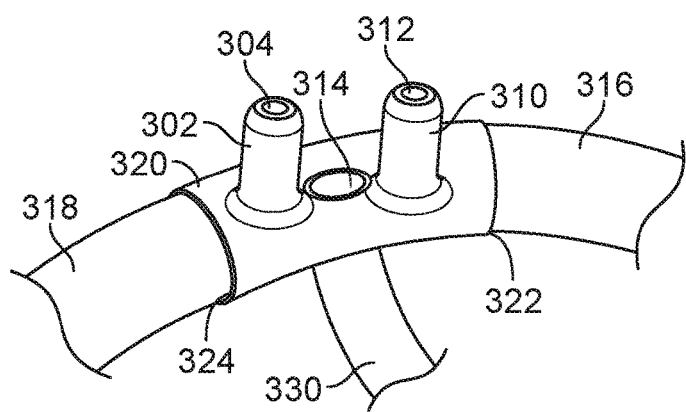
FIG. 4 shows another view of the nasal cannula of FIG. 3.

While the nasal cannula 100 of FIGS. 1 and 2 includes a third prong 113 protruding from the facepiece 120, in other implementations the medicament outlet may be formed as a slit in the facepiece. For example, FIG. 3 shows a top view of a nasal cannula 300 having a medicament outlet 314, and FIG. 4 shows a view of the nasal cannula 300. The nasal cannula 300 includes a first prong 302, a first outlet 304, a second prong 310, a second outlet 312, a medicament outlet 314, a facepiece 320, a first tube 316, a second tube 318 and a third tube 330. The first prong 302 has a first outlet 304, and the second prong 310 has a second outlet 312. The first outlet 304, the second outlet 312, and the medicament outlet 314 are all disposed substantially along a longitudinal axis 317 of the facepiece 320 such that the medicament outlet 314 is located substantially between the first and second prongs 302 and 310. The medicament outlet 314 is located between the first and second outlets 304 and 312 along the longitudinal axis 317 to facilitate entrainment of the aerosolized medicament into the flow of heated and humidified breathing gas and mixing of the aerosolized medicament and heated and humidified breathing gas just outside or within the nare. Though the medicament outlet 314 is shown as rectangular in FIG. 3, the medicament outlet can be circular, rectangular, or any other suitable shape having any suitable orientation and size.

The first tube 316 is connected to a first end 322 of the facepiece 320 and is in fluid communication with the first and second prongs 302 and 310. Similarly, the second tube 318 is connected to a second end 324 of the facepiece 320 and is also in fluid communication with the first and second prongs 302 and 310. The first and second tubes 316 and 318 deliver heated and humidified gas to the first and second prongs 302 and 310. In parallel, the first tube delivers aerosolized medicament to the medicament outlet 314. Placement of the medicament outlet 314 between the prongs facilitates entrainment and allows aerosolized medicament to be delivered by the slipstream effect into both nares rather than only one. Such a configuration may facilitate the delivery of the aerosolized medicament in the event that a single nare becomes occluded. While two tubes (e.g., first tube 316 and second tube 318) deliver heated and humidified gas in nasal cannula 300, in some implementations, a single tube provides the heated and humidified gas to both the first and second prongs 302. In such implementations, the tube for delivering the aerosolized medicament may extend through the facepiece 320 while remaining separate from the flow of heated and humidified gas, which may flow to the first and second prongs 302 and 310 through the remaining volume inside the facepiece.

Figure 5:
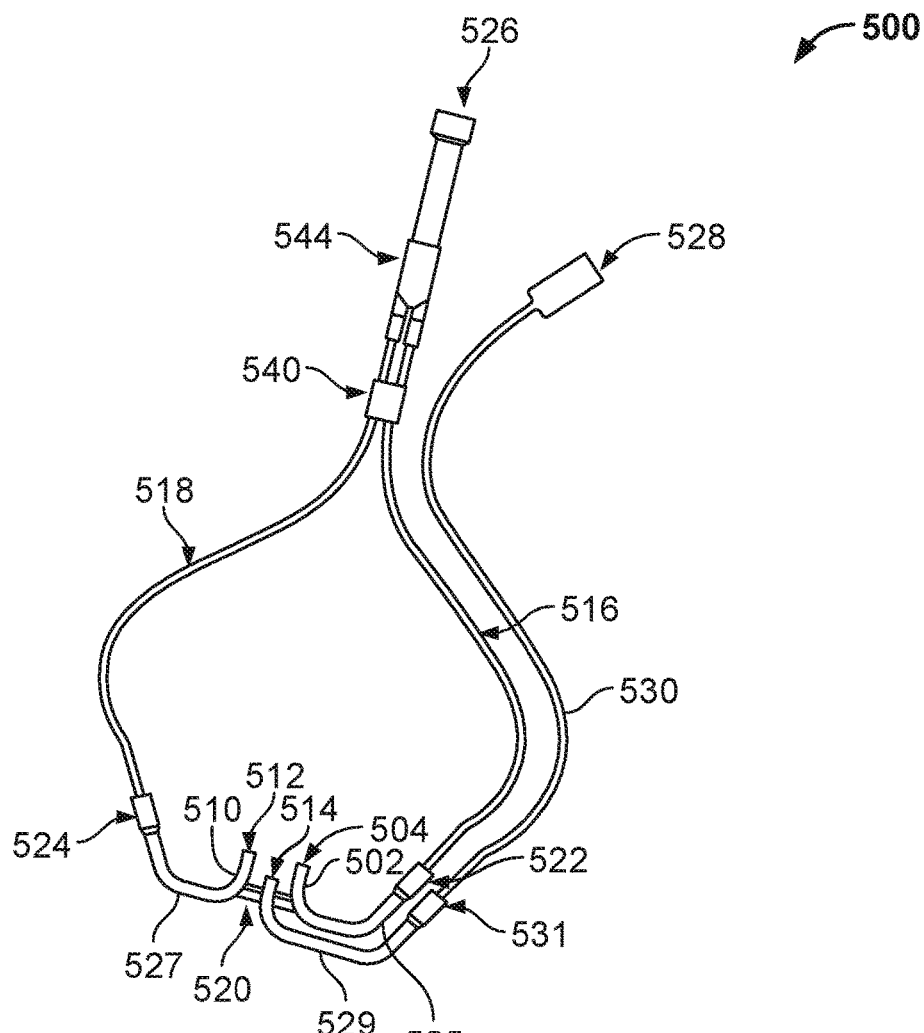
FIG. 5 shows an illustrative nasal cannula having separated prongs.

The nasal cannula 300 of FIG. 3 includes two nasal prongs (e.g., first prong 302 and second prong 310), which are in fluid communication at the facepiece 320. In some implementations, the flow paths to the first and second prongs are kept separate at the facepiece. For example, FIG. 5 shows a nasal cannula 500 having separated prongs 502 and 510. The nasal cannula 500 includes a first prong 502, a first outlet 504, a second prong 510, a second outlet 512, a medicament outlet 514, a first tube 516, a second tube 518, a third tube 530, a bridging element 520, a gas inlet 526, a splitter 544, a slider 540, a first molded facepiece 525, a second molded facepiece 527, and a third molded facepiece 529. The first prong 502 and the second prong 510 are each supplied with heated and humidified gas by the first tube 516 and second tube 518. The medicament outlet 514 is positioned between the first prong 502 and second prong 510 and is supplied with aerosolized medicament by the third tube 530. The heated and humidified gas is supplied at the inlet 526 which splits at the splitter 544 into two tubes, the first tube 516 and the second tube 518. The tubes (e.g., first tube 516 and second tube 518) are held together by the slider 540. The first tube 516 enters the first molded plastic facepiece 525 at a first end 522 and provides heated and humidified gas through the length of the first molded facepiece 525 to the first prong 502 and out the first outlet 504. The second tube 518 enters the second molded plastic facepiece 527 at a second end 524 and provides heated and humidified gas through the length of the second facepiece 527 to the second prong 510 and out the second outlet 512. The third tube 530 receives aerosolized medicament at an inlet 528 and connects to a third molded facepiece 529 at a third end 531. The aerosolized medicament flows to the medicament outlet 514 which is located between the first prong 502 and the second prong 510, held together by the bridging element 520. The positioning of the three outlets leads to a quieter cannula because the flows mix in the same direction rather than having flows with opposite directionalities mixing. In addition, the configuration of the three outlets enables a lower flow resistance which allows for use of a lower pressure gas source (e.g., a blower). The positioning of the medicament outlet 514 and the prongs 502 and 510 in relation to one another may be changed by adjusting the bridging element 520 to accommodate a wider range of patient sizes and anatomies.

Figure 6:
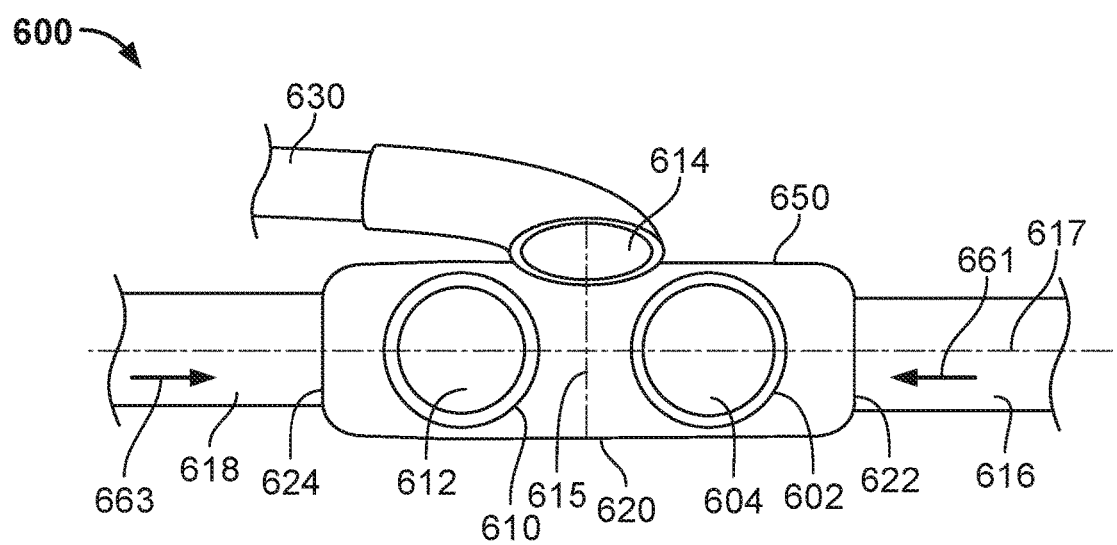
FIG. 6 shows a top view of an illustrative nasal cannula having a medicament outlet formed as a slit located dorsal to a pair of prongs.

While the nasal cannula 500 of FIG. 5 includes first and second prongs 502 and 510 in-line with the medicament outlet 514 along the facepiece 527, in some implementations, the medicament outlet may be positioned dorsal to the two prongs. For example, FIG. 6 shows a top view of an illustrative nasal cannula 600 having a medicament outlet 614 formed as a slit located dorsal to both the first and second prongs 602 and 610. The nasal cannula 600 includes a first prong 602, a first outlet 604, a second prong 610, a second outlet 612, a medicament outlet 614, a facepiece 620, a first tube 616 and a second tube 618. The first prong 602 and the second prong 610 may be located substantially along the longitudinal axis 617 of the facepiece 620, while the medicament outlet 614 is dorsal to the longitudinal axis 617. In this configuration, heated and humidified gas is provided to the first 604 and second outlets 612 by the first and second tubes 616 and 618, while the aerosolized medicament is provided to the medicament outlet 614 by the third tube 630. The positioning of the medicament outlet 614 facilitates entrainment of the aerosolized medicament in the flow of breathing gas from the first and second outlets 604 and 612.

The first tube 616 connects to the facepiece 620 at a first end 622 and provides the heated and humidified gas with a first directionality 661 to the first outlet 604. The second tube 618 connects to the facepiece 620 at a second end 624 and provides heated and humidified breathing gas with a second directionality 663 to the second outlet 612. In some implementations, there is a wall or partition 615 between the first prong 602 and the second prong 610 within the facepiece 620 to prevent turbulent mixing of the humidified air with the first directionality 661 and second directionality 663 before exiting through the outlets (e.g., first outlet 604 and second outlet 612). The third tube 630 is attached to an upper portion 650 of the facepiece 620. In some implementations, the third tube 630 is attached to the facepiece 620 at an end such as the second end 624 next to the connection to the second tube 618 for stability or may attach in any other suitable location. In certain implementations, the heated and humidified gas is provided to the first prong 602 and the second prong 610 by a single tube such that there are only two tubes in use, one carrying heated and humidified gas and the other carrying aerosolized medicament.

Figure 7:
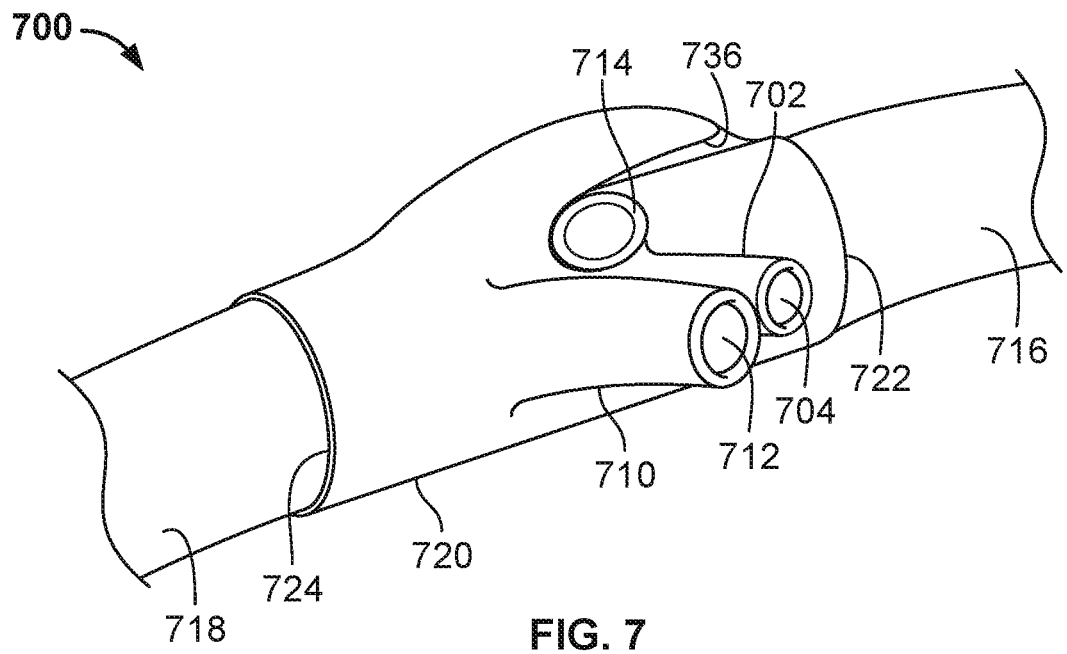
FIG. 7 shows an illustrative nasal cannula having a directional element to direct flow of the aerosolized medicament.

In some implementations in which the medicament outlet is formed as a slit in a facepiece rather than as a prong, it may be desirable to include an element to direct the flow of the aerosolized medicament from the medicament outlet into the slipstream produced by the humidified gas. For example, FIG. 7 shows a nasal cannula 700 similar to the nasal cannula 600, but including a directional element 736 to direct flow of the aerosolized medicament out of the medicament outlet 714. The nasal cannula 700 includes a first prong 702, a first outlet 704, a second prong 710, a second outlet 712, a facepiece 720, a medicament outlet 714, a directional element 736, a first tube 716, and a second tube 718. The medicament outlet 714 is a slit and is located above the first and second prongs 702 and 710. While the humidified breathing gas is supplied to nasal cannula 600 in FIG. 6 by two tubes, in the nasal cannula 700 of FIG. 7, a single tube 716 connected to the facepiece 720 at a first end 722 is used to supply humidified breathing gas to both prongs 702 and 710. A second tube 718 connected to the facepiece 720 at a second end 724 supplies aerosolized medicament to the medicament outlet 714. The aerosolized medicament is driven through the tube 718 from a nebulizer (not shown) but has a low flow rate and relies on the slipstream effect of the faster flowing heated and humidified breathing gas to carry it from the medicament outlet 714 and into the nare. The medicament outlet 714 includes a directional element 736 which directs the flow of medicament exiting the medicament outlet 714 toward the flow of humidified breathing gas out of the first outlet 704 and second outlet 712 to enhance the slipstream effect. The directional element 736 is shaped as a hood or a bill for the medicament outlet 714. This geometry directs the flow of medicament downwards to prevent aerosolized medicament from escaping above the patient's nares. Mixing of the aerosolized medicament with the heated and humidified breathing gas may occur between the outlets and the nares of a patient as well as just inside the nare. The use of the directional element 736 may be less intrusive than the use of a third prong because the directional element may be less likely to contact a patient's nose while still functioning to entrain the medicament into the slipstream of the aerosolized breathing gas for delivery to the patient.

Figure 8:
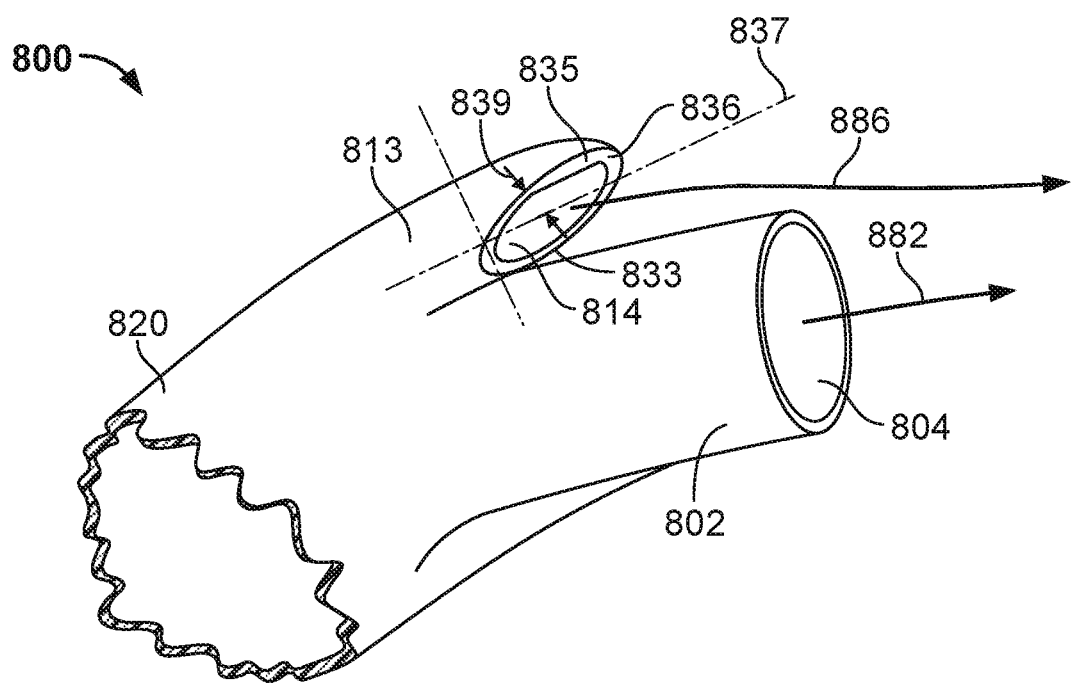
FIG. 8 shows a cut-away view of a nasal cannula having a prong with a directional element.

While the nasal cannula 700 includes a directional element 736 for a medicament outlet formed as a slit, a directional element can also be included in implementations in which the medicament outlet is included in a prong. For example, FIG. 8 shows a cut-away view of a nasal cannula 800 including a medicament outlet 814 having an overhanging guide piece 835. The nasal cannula 800 includes a breathing gas prong 802, a breathing gas outlet 804, a medicament prong 813 with a longitudinal axis 837, a medicament outlet 814, a lip 833, a directional element 836, and an overhanging guide piece 835. The medicament outlet 814 located on the prong 813 has a directional element 836 which extends beyond the lip 833 of the medicament outlet 814 to direct the flow of medicament 886 towards the flow of breathing gas 882. The directional element 836 may include an overhanging guide piece 835 which directs the flow of the aerosolized medicament and prevents loss of the medicament as the aerosolized medicament exits the medicament outlet 814. The overhanging guide piece 835 may be formed as a bill or hood which further directs the flow of the medicament 886. The overhanging guide piece 835 may extend beyond the lip of the outlet 833 by a short distance (e.g., 5 mm, 3 mm, 2 mm, 1 mm, or less) in order to direct the flow of the aerosolized medicament 886. The edges of the overhanging guide piece 835 may be tapered or curved or may form straight edges. The use of the directional element 836 with or without the use of the overhanging guide piece 835 improves the delivery of the aerosolized medicament to the patient and prevents loss of the medicament after the aerosol exits the outlet. In certain implementations, the directional element 836 may be created by fabricating the medicament outlet 814 such that the outlet 814 is not orthogonal to the longitudinal axis 837, but instead forms an oblique angle 839 with the longitudinal axis 837. This angle 839 can be chosen to direct the flow of the medicament to the nare or toward the flow of breathing gas 882. For example, the angle 839 may be 80°, 75°, 60°, 55°, 45°, 30°, or less to appropriately direct the flow of aerosolized medicament 886. Although the medicament outlet 814 is shown on a prong 813, the medicament outlet 814 and directional element 836 could be located on the body of the facepiece 820, on a protuberance from the facepiece 820, or in any other suitable location. Use of a directional element, such as 836 in the nasal cannula 800 and directional element 736 in the nasal cannula 700, to direct medicament flow into the slipstream can increase the efficiency with which the aerosolized medicament is delivered to the patient.

Figure 9:
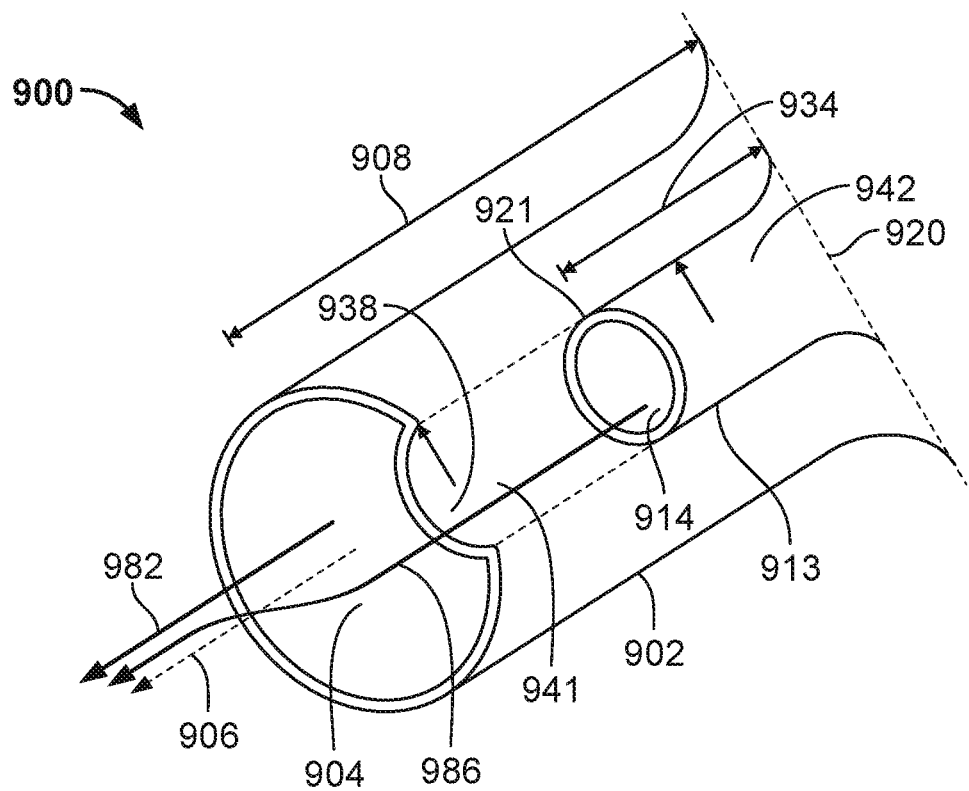
FIG. 9 shows an illustrative nasal prong having a groove located on its outer surface to direct the flow of the aerosolized medicament.

While the nasal cannulas 700 and 800 of FIGS. 7 and 8 have overhanging directional elements 736 and 836 incorporated into the medicament outlets 714 and 814 to direct the flow of medicament into the humidified gas stream, certain implementations may incorporate other features to direct the flow of aerosolized medicament into the flow of breathing gas. For example, FIG. 9 shows an illustrative nasal prong having a groove located on its outer surface to direct the flow of the aerosolized medicament 986. The cannula component 900 of FIG. 9 includes a first prong 902, a first outlet 904, a medicament prong 913, a medicament outlet 914, a facepiece 920 and a groove 941 formed in the first prong 902. The first prong 902 has an outlet 904 through which heated and humidified gas 982 flows. The prong 902 also has a longitudinal axis 906 and a length 908 in the direction of the longitudinal axis from the facepiece 920 to the outlet 904. The medicament prong 913 is located adjacent to the first prong 902 such that the medicament prong 913 and the first prong 902 share a common wall 921. The medicament prong 913 includes a medicament outlet 914. The medicament prong 913 has a second length 934 from the facepiece 920 to the outlet 914 which is shorter than the first length 908. The first prong 902 has a groove 941 in the side of the prong 902 along the common wall 921 with the medicament prong 913 to accommodate the medicament prong 913 and to direct the flow of the medicament 986 from the medicament outlet 914, along the groove 941, and into the flow of heated humidified gas 982 exiting the first outlet 904. The groove 941 in the side of the first prong 902 extends from the facepiece 920 to accommodate the medicament prong 913 and extends beyond the length 934 of the medicament prong 913 to the outlet 904. The groove 941 in the first prong 902 has a radius of curvature 938. The medicament prong 913 has a radius 942. In order to accommodate the flow of medicament from the medicament outlet 914, the radius of curvature 938 of the groove 941 may be substantially the same as or greater than the radius 942 of the medicament prong 913. The groove 941 in the side of the first prong 902 directs the flow of the medicament 986 along the side of the first prong 902 so that it will be included in the slipstream of the flow of heated and humidified gas 982 exiting the outlet of the first prong and carried into the nare. The groove 941 may be curved as shown here, or it may have a triangular cross section, a rectangular cross section, or any other suitable geometry for directing the flow of medicament.

Figure 10:
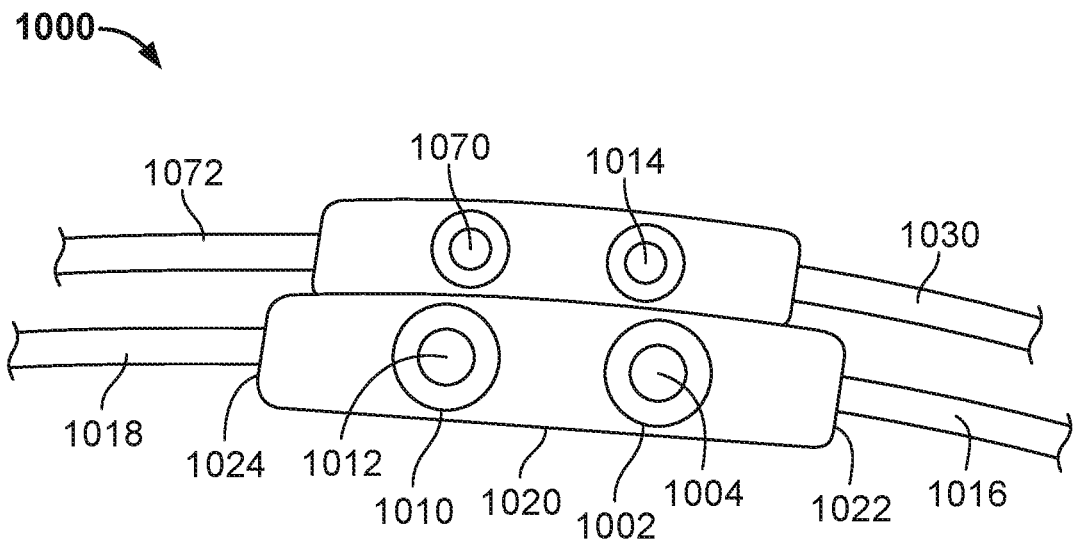
FIG. 10 shows a top view of a nasal cannula having two prongs delivering heated and humidified gas and two additional prongs delivering aerosolized medicament.

While the cannulas 100, 500, and 600 of FIGS. 1, 5 and 6 each have two prongs for supplying humidified breathing gas to the nares and a single medicament outlet (e.g. 114) supplying aerosolized medicament to the nares, in certain implementations aerosolized medicament may be supplied to the nares through two outlets. For example, FIG. 10 shows an illustrative implementation in which the cannula has two prongs 1002 and 1010 supplying heated and humidified breathing gas and two outlets 1014 and 1070 supplying aerosolized medicament to each of the nares. The cannula 1000 of FIG. 10 includes a first prong 1002, a first outlet 1004, a second prong 1010, a second outlet 1012, a first medicament outlet 1014, a second medicament outlet 1070, a facepiece 1020, a first tube 1016, a second tube 1018, a third tube 1030, and a fourth tube 1072. The first outlet 1004 and the second outlet 1012 deliver heated and humidified breathing gas to the nares, and the first medicament outlet 1014 and the second medicament outlet 1070 deliver aerosolized medicament to the nares. The heated and humidified gas is provided to the first outlet 1004 by the first tube 1016 connected to the facepiece 1020 at a first end 1022 and is provided to the second outlet 1012 by the second tube 1018 connected to the facepiece 1020 at a second end 1024. The aerosolized medicament is provided to the first medicament outlet 1014 by the third tube 1030 and to the second medicament outlet 1070 by the fourth tube 1072. The first medicament outlet 1014 and the second medicament outlet 1070 are located on the body of the facepiece 1020. In certain implementations, the first and second medicament outlets 1014 and 1070 are arranged on third and fourth prongs, respectively. In some implementations, the humidified gas is provided to both the first outlet 1004 and the second outlet 1012 by a single tube connected to the facepiece 1020 at one end. In some implementations, the aerosolized medicament from the first medicament outlet 1014 mixes with the heated and humidified gas from the first outlet 1004 within the nare of a patient. In certain implementations, the aerosolized medicament is provided to both the first 1014 and second medicament outlets 1070 by a single tube. Supplying aerosolized medicament to each of outlets 1014 and 1070 increases the likelihood that the medicament will be delivered to the patient even if one nare is occluded.

Figure 11:
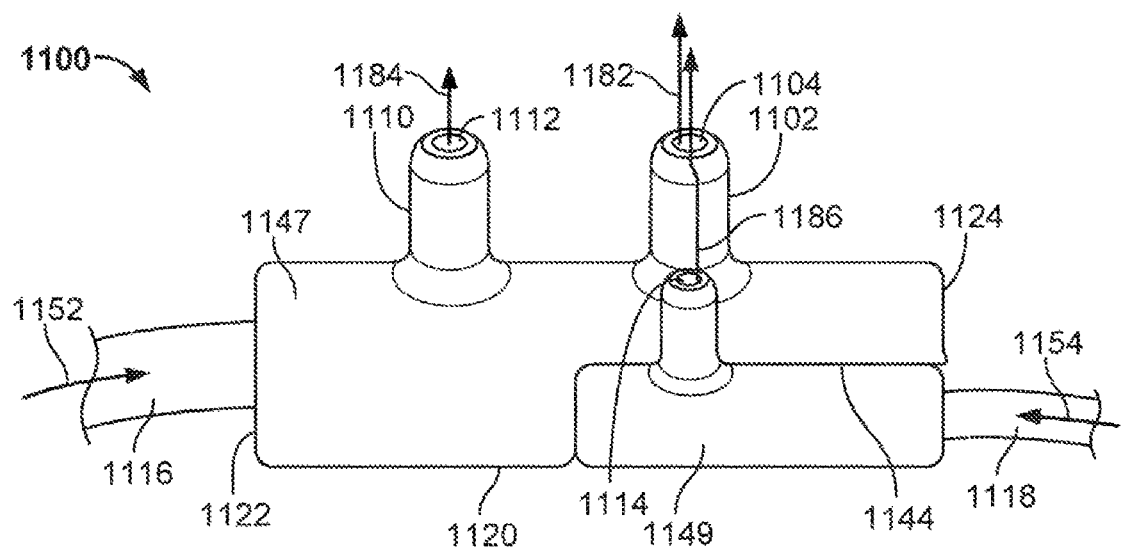
FIG. 11 shows an illustrative nasal cannula having a facepiece that is manufactured as two pieces which are joined.
Figure 12:
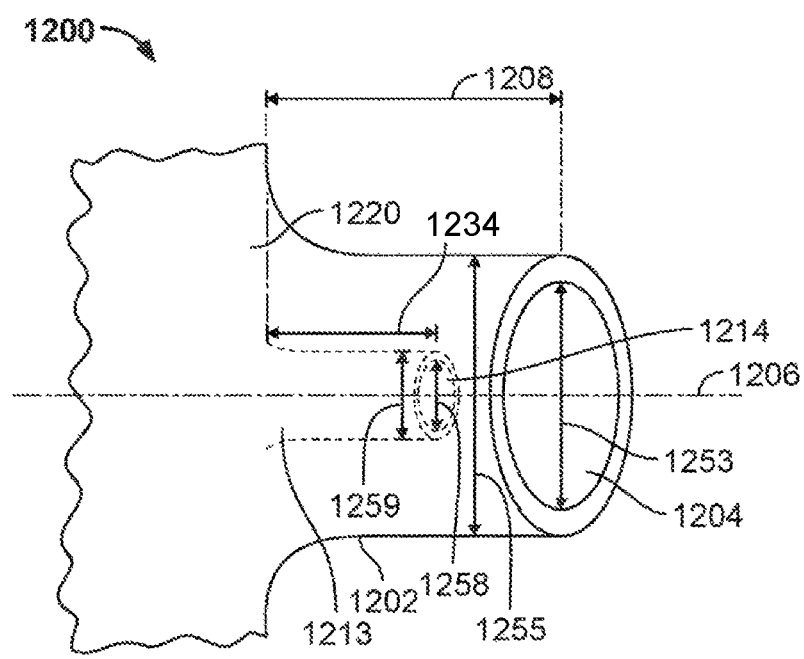
FIG. 12 shows an illustrative implementation in which the outlets for the medicament and heated and humidified gas are concentric, with the medicament outlet located inside the first prong.
Figure 13:
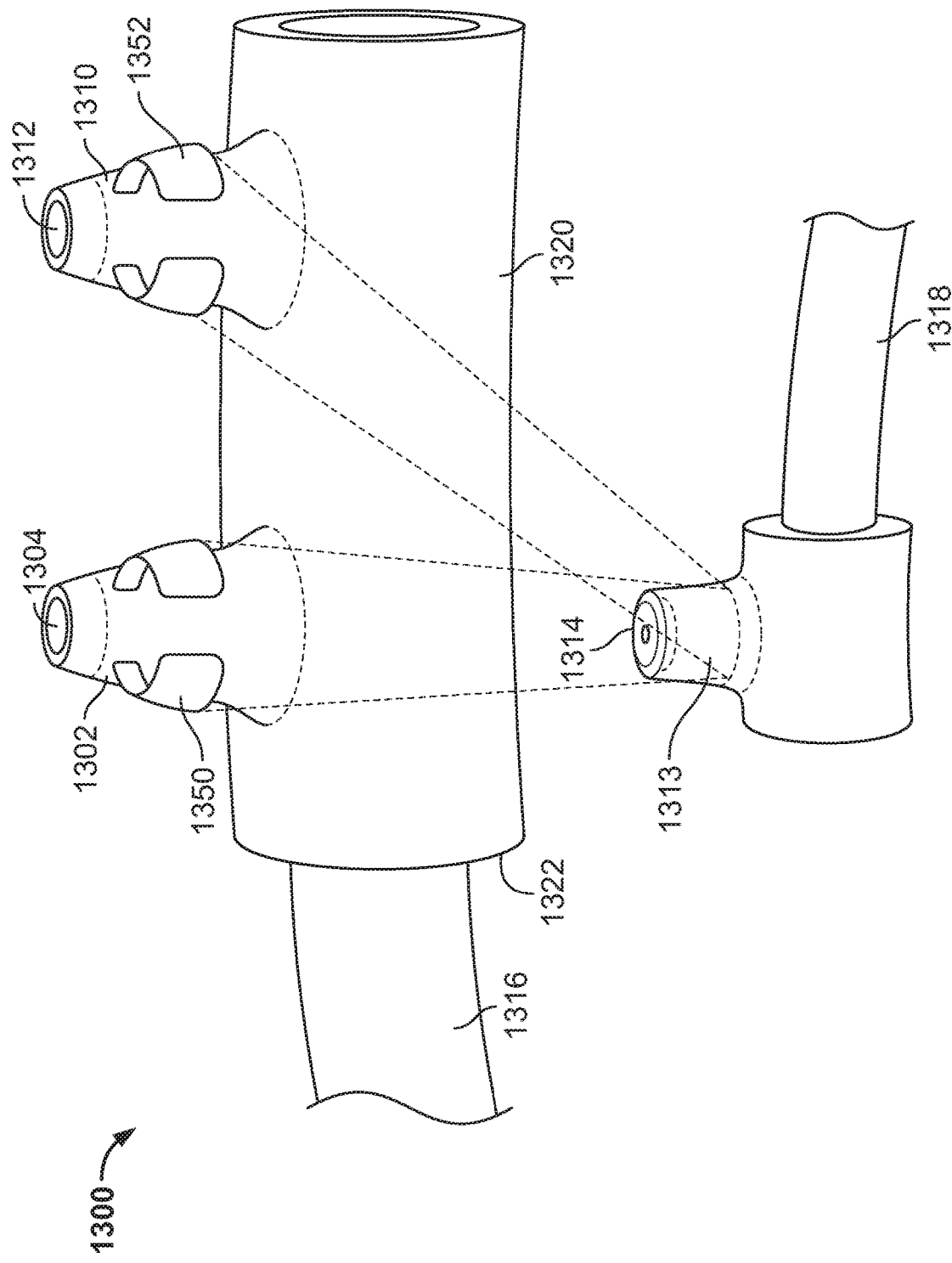
FIG. 13 shows an illustrative exploded view of a nasal cannula having two prongs delivering heated and humidified gas and an additional prong for delivery of the medicament attachable to either of the two prongs.

While the flow of the humidified gas and the aerosolized medicament are kept separate within the facepiece 120 by a partition 115 in the nasal cannula 100 of FIG. 2, in certain implementations the flows may be kept separate by constructing the facepiece from two separate components during fabrication of the nasal cannula. For example, FIG. 11 shows an illustrative nasal cannula having a facepiece 1120 fabricated as two components (e.g., first component 1147 and second component 1149), which are joined together. The cannula 1100 of FIG. 11 includes a first prong 1102, a first outlet 1104, a second prong 1110, a second outlet 1112, a first medicament outlet 1114, a facepiece 1120, a first tube 1116, a second tube 1118, a first component 1147 of the facepiece 1120, a second component 1149 of the facepiece 1120, and a common border 1144 between the facepiece components (e.g., first component 1147 and second component 1149). The first component 1147 of the facepiece 1120 includes the first and second prongs 1102 and 1110. The second component 1149 of the facepiece 1120 includes the first medicament outlet 1114. The flow of heated and humidified gas 1152 is provided from the first tube 1116 to the first component 1147 of the facepiece 1120 at a first end 1122. The heated and humidified gas exits the first prong 1102 through the first outlet 1104 as flow 1182 and exits the second prong 1110 through the second outlet 1112 as flow 1184. The flow of the aerosolized medicament 1154 is directed from the second tube 1118 coupled to the second component 1149 at a second end 1124 and exits the first medicament outlet 1114 as flow 1186. The separate components of the facepiece (e.g., first component 1147 and second component 1149) are fabricated separately and then joined to include a common border 1144 in order to keep the flow paths of the humidified gas and the aerosolized medicament separate until mixing occurs in the nare. The first component 1147 and second component 1149 can be joined by an adhesive, a weld, a fastener, a snap fit, an interference fit, or by any other suitable mechanism.

Although the nasal cannulas 100, 500, and 600 of FIGS. 1, 5, and 6 include medicament outlets which are adjacent to the breathing gas prongs and rely on the slipstream effect, in certain implementations the aerosolized medicament outlet may be located within a breathing gas prong to inject the aerosolized medicament directly into the flow of breathing gas. For example, FIG. 12 shows a nasal cannula 1200 in which the outlets for the medicament and heated and humidified gas are substantially concentric, with the medicament outlet 1214 located inside the first prong 1202. The nasal cannula 1200 of FIG. 12 includes a first prong 1202, a first outlet 1204, a second prong 1213, a medicament outlet 1214, and a facepiece 1220. The first prong 1202 has a longitudinal axis 1206 and a length 1208 in the direction of the longitudinal axis 1206. The second prong 1213 is located within the first prong 1202 and shares approximately the same longitudinal axis 1206. The second prong 1213 has a length 1234 in the direction of the longitudinal axis 1206 which is shorter than the length 1208 of the first prong 1202 such that the medicament outlet 1214 is entirely within the first prong 1402. The aerosolized medicament exits the medicament outlet 1214 and joins the flow of the heated and humidified gas, mixing with the heated and humidified gas within the first prong 1402. The first outlet 1204 has an inner diameter 1253 and an outer diameter 1255. Similarly, the medicament outlet 1214 has an inner diameter 1258 and an outer diameter 1259. The flow of the medicament from the facepiece 1220 to the medicament outlet 1214 is in substantially the same direction along the longitudinal axis 1206 as the flow of the heated and humidified gas from the first outlet 1204. Because the medicament outlet 1214 is located within the first prong 1202 and has a shorter height 1234, it is upstream from the first outlet 1202 with respect to the direction of the flow. In some implementations, the medicament outlet 1214 is offset by more than 1 mm and less than 3 cm along the longitudinal axis 1206. The inner diameter 1253 of the first prong 1202 is sized to accommodate the outer diameter 1259 of the medicament prong 1214.

The location of the medicament outlet 1214 within the first prong 1202 causes some mixing within the first prong 1202 rather than only in the nare external to the cannula after both flows have exited the medicament outlet 1214 and first outlet 1204, respectively. This may increase the temperature of the gas and aerosol mixture when it enters the nare, improving patient comfort. Though the medicament outlet 1214 is shown to be located concentrically within the prong 1202 and upstream from first outlet 1204 for the heated and humidified gas in FIG. 12, in some implementations, the first outlet 1204 is located concentrically within the medicament outlet 1214. In such implementations, the flow rate of the heated and humidified gas is increased by the use of a smaller radius of prong interior to the medicament. Placement of the medicament outlet 1214 concentrically within the first prong 1202 positions the medicament outlet 1214 to expel medicament directly into the flow of the humidified gas, increasing the amount of aerosolized medicament which enters the patient's nare.

While the nasal cannulas 100, 300, 500, 600, 800 and 1100 of FIGS. 1, 3, 5, 6, 8, and 11 each include an outlet for delivery of medicament, in certain implementations the medicament outlet can be detachably affixed at either of the nasal prongs. For example, FIG. 13 shows an illustrative exploded view in which the cannula has two prongs 1302 and 1310 supplying heated and humidified breathing gas and an outlet 1314 located on a third prong 1313 for supplying aerosolized medicament to the nare. The outlet may be affixed to either of two attachment points 1350 and 1352 on each of the first prong 1302 and second prong 1310. The cannula 1300 of FIG. 13 includes a first prong 1302, and first outlet 1304, a second prong 1310, a second outlet 1312, a third prong 1313, a first medicament outlet 1314, a facepiece 1320, a first connection point 1350, a second connection point 1352, a first tube 1316 and a second tube 1318. The first outlet 1304 and the second outlet 1312 deliver heated and humidified breathing gas to the nares, the first medicament outlet 1314 delivers aerosolized medicament to the nares. The first tube 1316 connected to the facepiece 1320 at a first end 1322 provides the heated and humidified breathing gas to the first prong 1302 and second prong 1310.

The second tube 1318 connected to the first medicament outlet 1314 provides aerosolized medicament to the first medicament outlet 1314. The first medicament outlet can be detachably affixed at the first connection point 1350 located at the first nasal prong 1302 or at a second connection point 1352 located at the second nasal prong 1310. The first medicament outlet 1314 can be detached from either of the first connection point 1350 and second connection point 1352. The first medicament outlet 1314 can be attached at either of the first connection point 1350 proximal to the first prong 1302 and second connection point 1352 proximal to the second prong 1310 such that the first medicament outlet 1314 delivers aerosolized medicament into the slipstream of the first prong 1302 or the second prong 1310. The first medicament outlet 1314 can be attached at the first connection point 1350 proximal to the first prong 1302 and can be detached from the first connection point 1350 and moved to the second connection point 1352 proximal to the second prong 1310, such that the first medicament outlet 1314 is moved from a first nare to the contralateral nare. The ability to move the first medicament outlet 1314 from the first prong 1302 to a second prong 1310 allows the continued delivery of medicament to a patient if one of the nares is occluded.

In some implementations, the first medicament outlet 1314 is attached at a first connection point 1350 located on a dorsal side of the first prong 1302. In other implementations, the first medicament outlet 1314 is inserted into the first prong 1302, such that the first prong 1302 surrounds the first medicament outlet 1314. In some implementations, the first connection point 1350 is configured as a clasp into which a side of the medicament outlet 1314 is inserted. In other implementations, the first connection point is configured as a restraining strap which is looped around the medicament outlet to restrain it into a position on the facepiece. For example, the strap may be a tape, a Velcro strap or any other suitable strap for restraining the medicament outlet 1314. In some implementations, the medicament outlet 1314 is located on a third prong configured to fit to the shape of the facepiece at either of the first prong 1302 or the second prong 1310, for example using a snap-fit.

Figure 14:
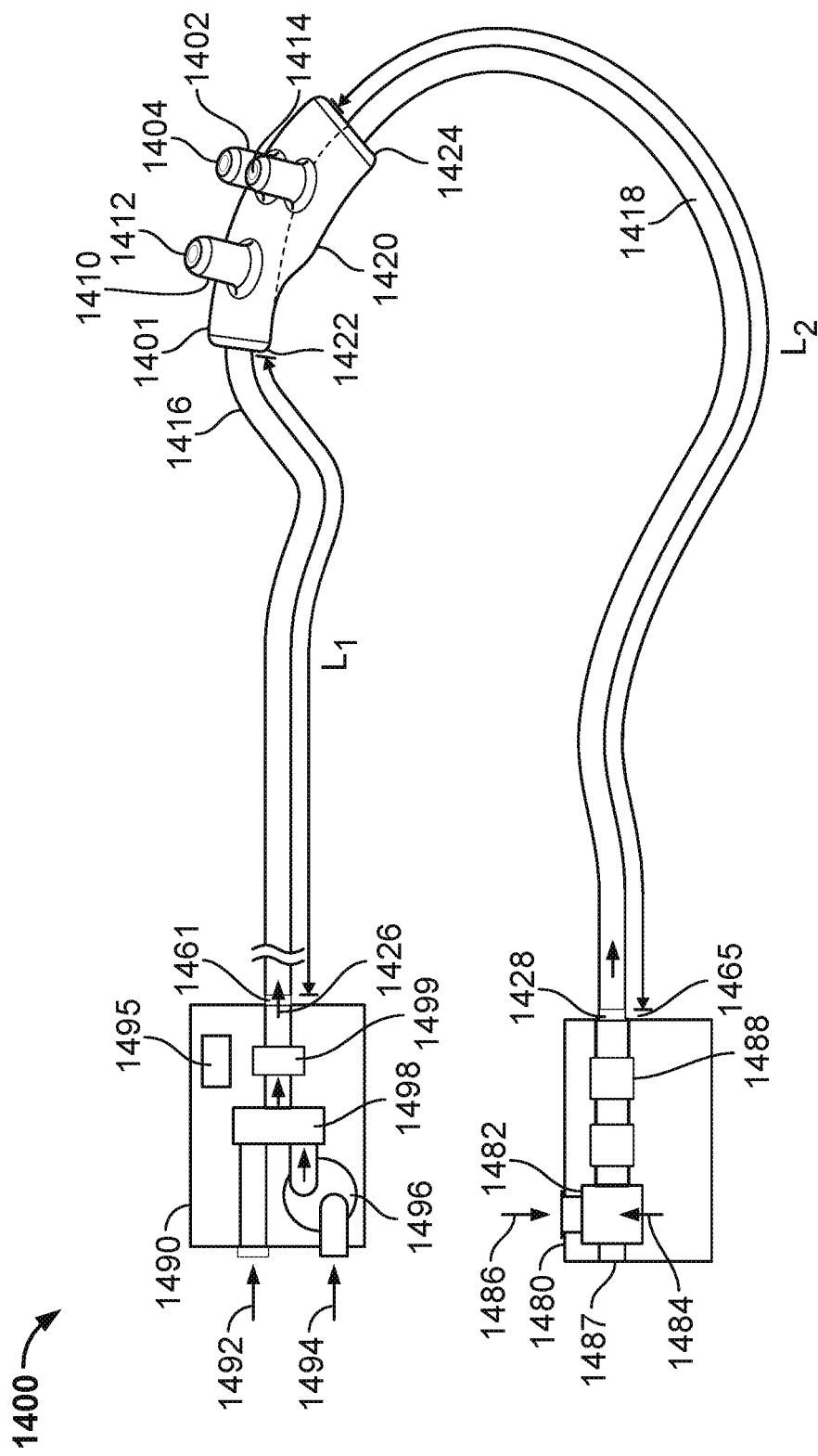
FIG. 14 shows an illustrative respiratory therapy system including a gas source, nebulizer and three-pronged cannula for simultaneous delivery of heated and humidified gas and aerosolized medicament.

The nasal cannulas described above can be incorporated into a respiratory therapy system, such as the illustrative respiratory therapy system 1400 shown in FIG. 14. The respiratory therapy system 1400 includes a gas source 1490, a nebulizer 1480, and a nasal cannula 1401 for simultaneous delivery of heated and humidified air together with aerosolized medicament. The gas source 1490 includes an oxygen inlet 1492 for receiving pressurized oxygen, an air inlet 1494 for receiving pressurized air, a compressor 1496, a gas blender 1498 and a gas heater and a humidifier 1499. The compressor 1496 is configured to pressurize the ambient air to output pressurized air at any suitable pressure (e.g., 0.5 psi, 1 psi, 2 psi, 5 psi, 10 psi, 20 psi, 40 psi, or 50 psi). The gas blender 1498 is configured to receive the pressurized air and oxygen and to output mixed gas. The gas heater 1499 is configured to heat the mixed output gas and output a heated breathing gas. The breathing gas source 1490 may also include a patient interface 1495 to allow a user to input various controls and display the temperature of the heated breathing gas exiting the gas outlet 1461. The breathing gas source 1490 includes a gas outlet 1461 which connects at a connector 1463 to an inlet 1426 of a first tube 1416. The tube 1416 connects the breathing gas source 1490 to the nasal cannula 1401, supplying the treated breathing gas to the patient along the first tube 1416 having a length L1.

The respiratory therapy system 1400 also includes a nebulizer unit 1480 which includes a liquid inlet 1486, a liquid reservoir 1482 holding a volume of liquid medicament 1484, an air inlet 1487 for compressed gas to aerosolize the liquid, and a passage 1488 to an outlet 1465 which connects to an inlet 1428 of a second tube 1418. The second tube 1418 supplies the aerosolized medicament to the nasal cannula 1401 along the tubing 1418 having length L2. L1 and L2 may be the same length or different lengths. L1 and L2 may be long enough to locate the gas source 1490 and nebulizer 1480 at a distance from the patient such that the noise associated with the gas source 1490 and nebulizer 1480 is decreased for the patient. L2 may be a large distance (e.g., 5 ft, 10 ft, 15 ft, 20 ft, 30 ft, 40 ft, or any other suitable length) which functions as a hanging volume of aerosolized medicament to stabilize the aerosol and increase efficacy of the medicament delivery to the patient. Large aerosol particles are likely to adhere to the sides of the tube 1418 along the length L2, and are thus less likely to reach the patient. Large aerosol particles often deposit in the upper respiratory tract, causing irritation and discomfort to the patient. Furthermore, these particles often do not reach the lower respiratory tract where the medicament is typically most needed. Thus, the removal of large aerosolized medicament particles results in a more uniform distribution of smaller sized particles which are able to reach the lower respiratory tract of a patient for effective delivery of medicament. Additionally, the second tubing 1418 with length L2 has an inner and outer diameter as shown in FIG. 1 as 164 and 166, respectively. The dimensions of the tubing 1418 supplying the aerosolized medicament to the nasal cannula 1401 may be adjusted in order to increase or decrease resistance and flow rate or to increase the hanging volume between the nebulizer 1480 and the patient.

The pressurized and treated breathing gas travels through the first tube 1416 with length L1 to arrive at the nasal cannula 1401. Meanwhile, the aerosolized medicament particles continuously flow from the nebulizer 1480 to the cannula 1401 through the second tube 1418 having length L2. The nasal cannula 1402 includes a facepiece 1420, a first prong 1402, a first outlet 1404, a second prong 1410, a second outlet 1412, a medicament outlet 1414, a first tube 1416, and a second tube 1418. The nasal cannula 1401 may have the features of any of the cannulas described herein or a combination thereof. The nasal cannula 1401 has a facepiece 1420 connected to the first tubing 1416 at a first end 1422 which supplies the breathing gas to the first and second prongs 1402 and 1410. The second tube 1418 having length L2 is connected to the facepiece 1420 at a second end 1424 and supplies aerosolized medicament to the medicament outlet 1414. Supplying aerosolized medicament and breathing gas to the nasal cannula 1401 by two separate lengths of tubing L1 and L2 allows the gas source 1490 and the nebulizer 1480 to be located at a distance from the patient so that the patient is more comfortable without the noise or bulk of these instruments nearby. The separate lengths of tubing 1416 and 1418 keep the aerosolized medicament and the breathing gas separate until mixing in the nare or just prior to entering the nare. The separation of the aerosol and gas decrease incidence of condensation of the humidified gas as it cools. The condensation of the humidified gas can trap aerosolized medicament particles in the condensate. Thus, by preventing the mixing of the humidified gas and aerosol along the flow path, the amount of aerosol delivered to the patient is increased.

FIG. 15 shows an illustrative process 1500 for delivering heated and humidified breathing gas together with aerosolized medicament to a patient. The process 1500 can be performed using any of the nasal cannulas described herein. It will be understood by one of ordinary skill in the art that, in addition to the steps shown in FIG. 15, a heated and humidified breathing gas and an aerosolized medicament may be generated for delivery to a patient by any suitable means.

In step 1502, heated and humidified breathing gas is passed through a first conduit, such as a length of tubing 1416, to a first outlet and a second outlet of a nasal cannula, such as nasal cannula 100, 300, 500, 600, 700, 800, 900, 1000, 1100, 1200, 1300, or 1401. The breathing gas may be supplied to the cannula through a length of tubing L1 from a gas source, such as gas source 1490. Additionally, the tubing may be attached to the facepiece of the nasal cannula, which includes a first prong and a second prong for supplying the breathing gas to the nares of a patient. In such cases, the breathing gas may flow through the tubing into the facepiece and out through the outlets and located on the prongs 1302 and 1410. The rate at which the heated and humidified breathing gas is passed through the first conduit may vary. For example, the heated and humidified breathing gas may pass through the first conduit at a rate of about 8 LPM or greater.

In step 1504, an aerosolized medicament is passed through a second conduit, such as a length of tubing, to a third outlet of the nasal cannula. The rate at which the aerosolized medicament is passed through the second conduit may vary. For example, aerosolized medicament may pass through the second conduit at a rate of about 2 LPM or less. The aerosolized medicament may be delivered from a source, such as a nebulizer, distal from the patient. The aerosolized medicament may then flow through a length of tubing L2 to the facepiece of the nasal cannula. The facepiece may include a wall or partition which keeps the aerosolized medicament separated from the breathing gas. The length of tubing may also attach to the outside of the facepiece. The aerosolized medicament is passed from the tubing to a third outlet which is directed toward a nare of a patient in order to supply medicament to the patient. In some implementations, the second conduit may have a length of about 10 cm or greater. Additionally or alternatively, the third outlet may be adjacent to the first outlet and aligned substantially parallel to the first outlet.

The heated and humidified gas of step 1502 and the aerosolized medicament of step 1504 are not in fluid communication along the length of their respective tubes. The heated and humidified breathing gas mixes with the aerosolized medicament upon exiting the cannula. After exiting, the aerosolized medicament is entrained by the flow of the heated and humidified gas. The medicament outlet may be positioned in order to expel the aerosolized medicament into the slipstream of the high flow heated and humidified gas. The medicament is then borne into the nare by the slipstream effect.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy systems, may be applied to systems, devices, and methods to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A nasal cannula for delivering humidified breathing gas and nebulized medication, the nasal cannula comprising:
   a first prong having a first outlet, a longitudinal axis, and a first length along the longitudinal axis;
   a second prong having a second outlet;
   a third prong having a third length, disposed on an outer surface of the first prong, and comprising a first medicament outlet configured to pass aerosolized medicament substantially parallel to the longitudinal axis, the third prong extending alongside the first prong and sharing a common wall with the first prong such that breathing gas and medicament flows are separated by the common wall, wherein the third length is less than the first length of the first prong;
   a first tube having a first inlet for receiving breathing gas, the first tube being in fluid communication with the first and second prongs; and
   a second tube having a second inlet for receiving the aerosolized medicament, the second tube being in fluid communication with the first medicament outlet;
   wherein the first tube is not in fluid communication with the second tube along a second length of the second tube; and
   wherein the cannula is configured such that during operation a velocity of the humidified breathing gas exiting the first outlet is greater than a velocity of the aerosolized medicament exiting the first medicament outlet.

2. The nasal cannula of claim 1, wherein the first medicament outlet is offset from the first outlet along the longitudinal axis.

3. The nasal cannula of claim 2, wherein the first medicament outlet is upstream from the first outlet with respect to a direction of breathing gas flow through the first outlet.

4. The nasal cannula of claim 3, wherein the first medicament outlet is offset by more than 1 mm and less than 3 cm along the longitudinal axis.

5. The nasal cannula of claim 4, wherein the first medicament outlet is configured to mix a first flow of the aerosolized medicament with the breathing gas flow through the first outlet downstream from the first outlet.

6. The nasal cannula of claim 1, wherein the third prong is integrally formed on the first prong along the common wall.

7. The nasal cannula of claim 1, further comprising a second medicament outlet disposed adjacent to the second prong and arranged to pass the aerosolized medicament substantially parallel to the longitudinal axis.

8. The nasal cannula of claim 1, wherein the first prong and the second prong extend from a facepiece, the facepiece being substantially orthogonal to the longitudinal axis and having a first end and a second end opposite the first end.

9. The nasal cannula of claim 8, wherein the first tube is coupled to the first end and the second tube is coupled to the second end.

10. The nasal cannula of claim 8, wherein the medicament outlet is disposed on the facepiece between the first prong and the second prong.

11. The nasal cannula of claim 1, wherein the second tube has an internal diameter of 5 mm or more.

12. The nasal cannula of claim 11, wherein the second tube has an internal diameter of 10 mm or more.

13. The nasal cannula of claim 1, wherein the second length of the second tube is 20 cm or more.

14. The nasal cannula of claim 1, wherein the second tube has an internal volume of 20 cm$^3$ or greater.

15. The nasal cannula of claim 1, wherein the second tube has an internal volume of 70 cm$^3$ or greater.

16. The nasal cannula of claim 1, wherein the first outlet has a first cross-sectional area and the first medicament outlet has a second cross-sectional area, wherein the second cross-sectional area is less the first cross-sectional area.

17. The nasal cannula of claim 16, wherein the second cross-sectional area is one third of the first cross-sectional area or greater.

18. The nasal cannula of claim 1, wherein a flow resistance from the second inlet to the first medicament outlet is less than 1 psi at a flow rate of 1 LPM.

19. The nasal cannula of claim 1, wherein the third prong is arranged to be detachably affixed to either the first prong or the second prong.

20. The nasal cannula of claim 19, wherein the first prong comprises a first connection point and the second prong comprises a second connection point, such that the third prong is arranged to be detachably affixed to either the first prong via the first connection point or the second prong via the second connection point.

21. The nasal cannula of claim 20, wherein the first connection point is located on a dorsal side of the first prong, and the second connection point is located on a dorsal side of the second prong.

22. The nasal cannula of claim 1, wherein the first medicament outlet comprises a directional element arranged to extend beyond a lip of the first medicament outlet to direct the aerosolized medicament towards a slipstream of breathing gas.

23. A method for delivering humidified breathing gas and nebulized medication, the method comprising:

passing heated and humidified breathing gas through a first conduit to a first outlet and a second outlet of a nasal cannula, the first conduit having a first length; and passing an aerosolized medicament through a second conduit to a third outlet, the second conduit having a second length of 10 cm or greater, wherein the third outlet is disposed on an outer surface of the first outlet and is configured to pass aerosolized medicament substantially parallel to the longitudinal axis, the third outlet extending alongside the first outlet and sharing a common wall with the first outlet such that breathing gas and medicament flows are separated by the common wall, the second length being less than the first length;

wherein, the heated and humidified breathing gas mixes with the aerosolized medicament after exiting the nasal cannula; and wherein a velocity of the humidified breathing gas exiting the first outlet is greater than a velocity of the aerosolized medicament exiting the third outlet.

24. The method of claim 23, wherein the second conduit is not in fluid communication with the first conduit along the first length of the first conduit.

25. The method of claim 24, wherein the third outlet is offset from the first outlet along a longitudinal axis of the first outlet.

26. The method of claim 25, wherein the aerosolized medicament is entrained by the flow of heated and humidified breathing gas out of the first outlet.

27. The method of claim 23, wherein the heated and humidified breathing gas is passed through the first conduit at a rate of 8 LPM or greater.

28. The method of claim 27, wherein the aerosolized medicament is passed through the second conduit at a rate of 2 LPM or less.

29. The method of claim 23, wherein an inlet of the first conduit is adjacent to an inlet of the second conduit.

30. A respiratory therapy system for delivering humidified breathing gas and nebulized medication, the system comprising:

a nasal cannula including:

a first prong having a first outlet and a longitudinal axis;

a second prong having a second outlet;

a third prong having a third length, disposed on an outer surface of the first prong, and comprising a first medicament outlet configured to pass aerosolized medicament substantially parallel to the longitudinal axis, the third prong extending alongside the first prong and sharing a common wall with the first prong such that breathing gas and medicament flows are separated by the common wall, wherein the third length is less than the first length of the first prong;

a first tube in fluid communication with the first and second prongs; and a second tube having a second length, wherein the first tube is not in fluid communication with the second tube along a length of the first tube;

a nebulizer in fluid communication with the first medicament outlet through the second tube; and wherein the respiratory therapy system is configured such that during operation a velocity of the humidified breathing gas exiting the first outlet is greater than a velocity of the aerosolized medicament exiting the first medicament outlet.

31. The system of claim 30, further comprising a source of pressurized driving gas in fluid communication with the second tube, wherein the source of pressurized driving gas supplies gas that carries the aerosolized medicament to the patient.

32. The system of claim 30, further comprising a source of heated and humidified breathing gas in fluid communication with the first and second prongs.

33. The system of claim 30, wherein the first medicament outlet is offset from the first outlet along the longitudinal axis.

34. The system of claim 30, wherein the first medicament outlet is configured to mix a first flow of the aerosolized medicament with a second flow of breathing gas downstream from the first outlet.

35. The system of claim 30, further comprising a second medicament outlet disposed adjacent to the second prong and arranged to pass the aerosolized medicament substantially parallel to the longitudinal axis.

36. The system of claim 30, wherein the first prong and the second prong extend from a facepiece, the facepiece being substantially orthogonal to the longitudinal axis and having a first end and a second end opposite the first end.

37. The system of claim 36, wherein the first tube is coupled to the first end and the second tube is coupled to the second end.

38. The system of claim 30, wherein the second tube has an internal diameter of 5 mm or more.

39. The system of claim 30, wherein the second length of the second tube is 2 feet or more.

40. The system of claim 30, wherein the second tube has an internal volume of 20 $cm^3$ or greater.

* * * * *